US009589108B2

(12) United States Patent
Blom et al.

(10) Patent No.: US 9,589,108 B2
(45) Date of Patent: *Mar. 7, 2017

(54) METHOD AND APPARATUS FOR TRACKING AND DISSEMINATING HEALTH INFORMATION VIA MOBILE CHANNELS

(71) Applicant: Nokia Corporation, Espoo (FI)

(72) Inventors: Jan Otto Blom, Lutry (CH); Dhaval Jitendra Joshi, Bangalore (IN)

(73) Assignee: Nokia Technologies Oy, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 14/852,179

(22) Filed: Sep. 11, 2015

(65) Prior Publication Data
US 2015/0379240 A1 Dec. 31, 2015

Related U.S. Application Data

(63) Continuation of application No. 13/394,022, filed on Jun. 15, 2012, now Pat. No. 9,171,451, which is a (Continued)

(30) Foreign Application Priority Data

Sep. 2, 2009 (IN) .......................... 1808/DEL/2009

(51) Int. Cl.
H04M 11/04 (2006.01)
G06F 19/00 (2011.01)
(Continued)

(52) U.S. Cl.
CPC ....... *G06F 19/3493* (2013.01); *G08B 27/005* (2013.01); *G08B 27/006* (2013.01);
(Continued)

(58) Field of Classification Search
CPC . G06F 19/3493; G08B 27/005; G08B 27/006; H04W 4/021; H04W 4/185;
(Continued)

(56) References Cited

U.S. PATENT DOCUMENTS 6,028,514 A 2/2000 Lemelson et al.
6,745,021 B1 6/2004 Stevens
(Continued)

FOREIGN PATENT DOCUMENTS

EP 1 143 758 A1 10/2001
WO 03/061452 A2 7/2003
(Continued)

OTHER PUBLICATIONS

Office Action for corresponding European Patent Application No. 10813388.5-1803, dated Mar. 29, 2016, 4 Pages.
(Continued)

Primary Examiner — Mong-Thuy Tran
(74) Attorney, Agent, or Firm — Ditthavong & Steiner, P.C.

(57) ABSTRACT

An approach is provided for tracking and disseminating health information. Health information corresponding to a geographic location is caused, at least in part, to be received. Location information associated with a user equipment configured to receive a message specifying content is determined. Whether the location information is encompassed by the geographic location is determined. The message is modified to present a health alert indicator by appending supplemental content to the message or by amending the content. Initiation of delivery of the modified message to the user equipment when the user equipment is in or within a predetermined range of the geographic location is caused, at least in part.

6 Claims, 13 Drawing Sheets

Related U.S. Application Data continuation of application No. PCT/FI2010/050663, filed on Aug. 25, 2010.

(51) Int. Cl.
| | |
|---|---|
| *G08B 27/00* | (2006.01) |
| *H04W 4/18* | (2009.01) |
| *H04W 4/02* | (2009.01) |
| *H04W 4/22* | (2009.01) |

(52) U.S. Cl.
CPC .......... *H04W 4/021* (2013.01); *H04W 4/185* (2013.01); *H04W 4/22* (2013.01)

(58) Field of Classification Search
CPC .... H04W 4/22; H04W 24/00; H04L 67/2804; H04M 11/04
USPC ................. 455/404.2, 404.1, 456.1
See application file for complete search history.

(56) References Cited

U.S. PATENT DOCUMENTS

| | | |
|---|---|---|
| 7,109,859 B2 | 9/2006 | Peeters |
| 7,343,302 B2 | 3/2008 | Aratow et al. |
| 7,660,397 B2 | 2/2010 | Heen et al. |
| 7,705,723 B2 | 4/2010 | Kahn et al. |
| 8,010,380 B2 | 8/2011 | Kanaan |
| 8,392,152 B2 | 3/2013 | Rao |
| 8,405,503 B2 | 3/2013 | Wong |
| 8,684,923 B2 | 4/2014 | Craine et al. |
| 2003/0129578 A1 | 7/2003 | Mault |
| 2003/0177038 A1 | 9/2003 | Rao |
| 2003/0204130 A1 | 10/2003 | Colston, Jr. et al. |
| 2004/0116821 A1 | 6/2004 | Beiswenger et al. |
| 2006/0036619 A1 | 2/2006 | Fuerst et al. |
| 2006/0040639 A1* | 2/2006 | Karl ............ G08B 27/006 455/404.1 |
| 2006/0223492 A1* | 10/2006 | Chin ............ H04L 12/1895 455/404.1 |
| 2006/0234672 A1* | 10/2006 | Adler ............ G08B 27/003 455/404.1 |
| 2007/0198299 A1 | 8/2007 | Puckrein |
| 2007/0202927 A1* | 8/2007 | Pfleging ......... G08B 27/001 455/567 |
| 2007/0216535 A1 | 9/2007 | Carrino |
| 2007/0229290 A1* | 10/2007 | Kahn ............ G06F 19/3493 340/573.4 |
| 2008/0004798 A1* | 1/2008 | Troxler .......... A01K 15/023 702/187 |
| 2008/0208620 A1 | 8/2008 | Karkanias et al. |
| 2009/0005067 A1 | 1/2009 | Ernst et al. |
| 2009/0049140 A1 | 2/2009 | Stoddard et al. |
| 2009/0076851 A1 | 3/2009 | Rao |
| 2009/0182551 A1 | 7/2009 | Cao |
| 2009/0216747 A1 | 8/2009 | Li et al. |
| 2009/0216775 A1* | 8/2009 | Ratliff .......... G06Q 10/08 |
| 2009/0224881 A1 | 9/2009 | Koon et al. |
| 2009/0319295 A1* | 12/2009 | Kass-Hout ......... G06F 19/3493 705/2 |
| 2009/0325538 A1 | 12/2009 | Sennett et al. |
| 2010/0316196 A1 | 12/2010 | Jokinen |
| 2013/0132993 A1 | 5/2013 | Huchital et al. |

FOREIGN PATENT DOCUMENTS

| | | |
|---|---|---|
| WO | 2007106588 A2 | 9/2007 |
| WO | 2009/087269 A1 | 7/2009 |
| WO | 2009/155704 A1 | 12/2009 |

OTHER PUBLICATIONS

Office Action for corresponding Chinese Patent Application No. 201080045803.9, dated Apr. 5, 2016, 12 Pages, English Language Summary Included.
Office Action for corresponding Chinese Patent Application No. 201080045803.9, dated Apr. 3, 2015, with English language summary, 10 Pages.
Office Action for corresponding Chinese Patent Application No. 201080045803.9 dated Oct. 24, 2014, with English-language summary, 7 Pages.
Office Action for corresponding Chinese Patent Application No. 201080045803.9 dated Apr. 23, 2014, with English language summary, 10 Pages.
Office Action for corresponding European Patent Application No. 10813388.5, dated Feb. 1, 2013, pp. 1-11.
International Search Report for International Application No. PCT/FI2010/050663, dated Dec. 30, 2010, 4 pages.
Written Opinion of the International Searching Authority for International Application No. PCT/FI2010/050663, dated Dec. 30, 2010, 8 pages.
Office Action for corresponding Chinese Patent Application No. 201080045803.9 dated Oct. 20, 2015, with English-language summary, 12 Pages.

* cited by examiner

| | PHONE NUMBER | PRIMARY HEALTH CENTER LOCATION |
|---|---|---|
| 401 | 9900455543 | DISTRICT A, CITY A |
| 403 | 9300444444 | DISTRICT A, CITY A |
| 405 | 3200555555 | DISTRICT A, CITY A |
| 407 | 9900666666 | DISTRICT B, CITY A |
| 409 | 4900777777 | DISTRICT B, CITY A |
| 411 | 9901888888 | DISTRICT C, CITY A |
| 413 | 9901999999 | DISTRICT C, CITY A |
| 415 | 9400555555 | DISTRICT A, CITY A |
| 417 | 9800555555 | DISTRICT A, CITY A |

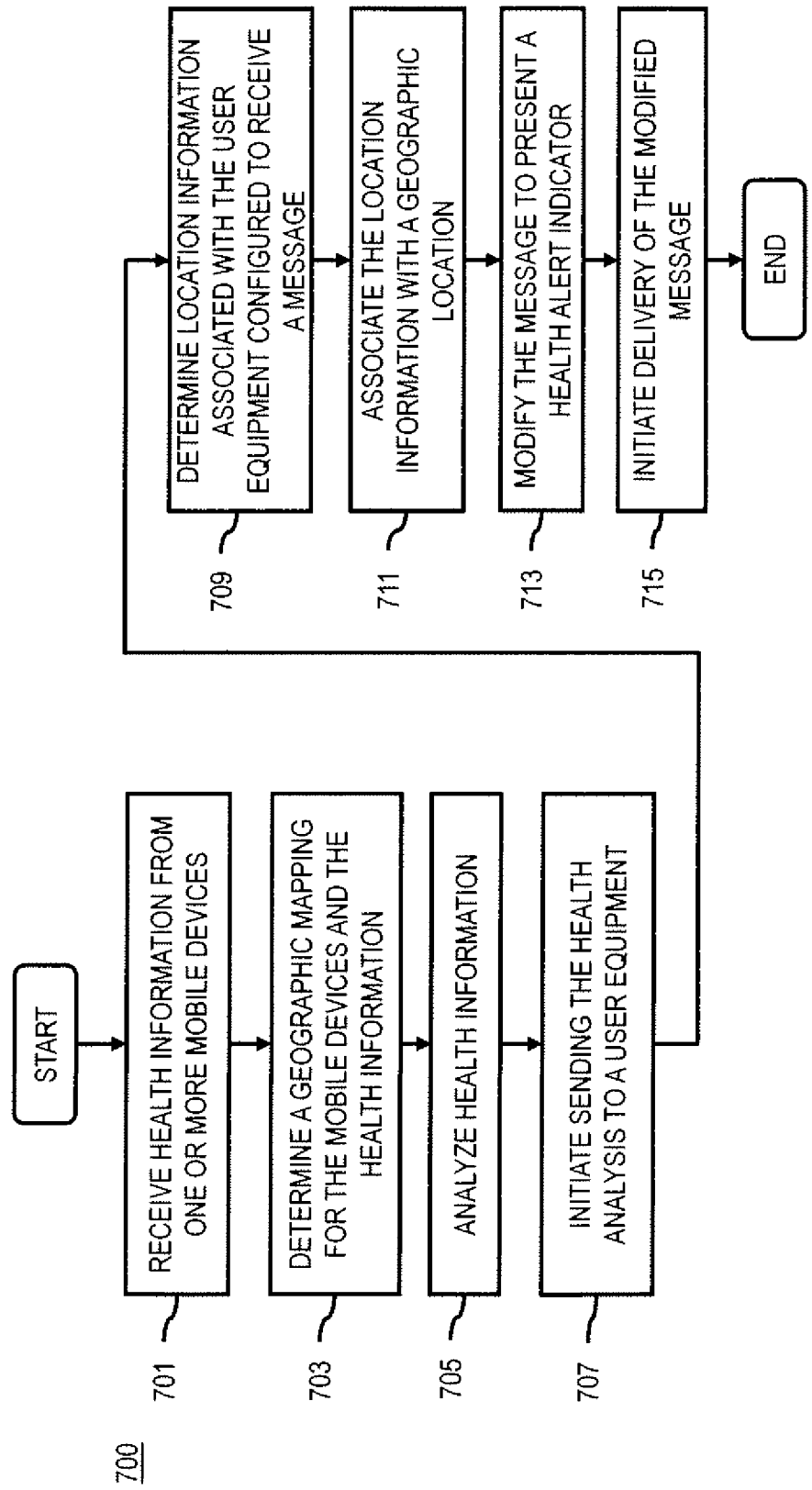

METHOD AND APPARATUS FOR TRACKING AND DISSEMINATING HEALTH INFORMATION VIA MOBILE CHANNELS

CROSS-REFERENCE TO RELATED APPLICATIONS

This application is a continuation of U.S. application Ser. No. 13/394,022, filed Jun. 15, 2012, which is a continuation of U.S. National Stage Application No. PCT/FI10/50663, filed Aug. 25, 2010, the entirety of which is incorporated herein.

BACKGROUND

Telecommunication technologies have been relatively underutilized in the health and medical services industry. For example, organizations have relied on collecting information from hospitals and clinics dispersed among various region to track the occurrence and spread of diseases. Traditionally the gathering and dissemination of health related information have been slow and ineffectual, in that such information can be manually intensive, and once the data has been collected and analyzed, the health treat (and thus prevention measures) may be moot.

Moreover, service providers (e.g., wireless, cellular, etc.) and device manufacturers are continually challenged to deliver value and convenience to consumers by, for example, providing compelling network services. In this regard, the health and medical services area has garnered some attention.

SOME EXAMPLE EMBODIMENTS

According to one embodiment, a method comprises causing, at least in part, receiving health information corresponding to a geographic location. The method also comprises determining location information associated with a user equipment configured to receive a message specifying content. The method further comprises determining whether the location information is encompassed by the geographic location. The method additionally comprises modifying the message to present a health alert indicator by appending supplemental content to the message or by amending the content; and causing, at least in part, initiating delivery of the modified message to the user equipment when the user equipment is in or within a predetermined range of the geographic location.

According to another embodiment, an apparatus comprising at least one processor, and at least one memory including computer program code, the at least one memory and the computer program code configured to, with the at least one processor, cause the apparatus to cause, at least in part, receiving health information corresponding to a geographic location. The apparatus is also caused to determine location information associated with a user equipment configured to receive a message specifying content. The apparatus is further caused to determine whether the location information is encompassed by the geographic location. The apparatus is further caused to modify the message to present a health alert indicator by appending supplemental content to the message or by amending the content; and cause, at least in part, initiating delivery of the modified message to the user equipment when the user equipment is in or within a predetermined range of the geographic location.

According to another embodiment, a computer-readable storage medium carrying one or more sequences of one or more instructions which, when executed by one or more processors, cause an apparatus to cause, at least in part, receiving health information corresponding to a geographic location. The apparatus is also caused to determine location information associated with a user equipment configured to receive a message specifying content. The apparatus is further caused to determine whether the location information is encompassed by the geographic location. The apparatus is further caused to modify the message to present a health alert indicator by appending supplemental content to the message or by amending the content; and cause, at least in part, initiating delivery of the modified message to the user equipment when the user equipment is in or within a predetermined range of the geographic location.

According to another embodiment, an apparatus comprises means for causing, at least in part, receiving health information corresponding to a geographic location; means for determining location information associated with a user equipment configured to receive a message specifying content; means for determining whether the location information is encompassed by the geographic location; means for modifying the message to present a health alert indicator by appending supplemental content to the message or by amending the content; and means for causing, at least in part, initiating delivery of the modified message to the user equipment when the user equipment is in or within a predetermined range of the geographic location.

According to one embodiment, a method comprises causing, at least in part, initiating presentation of a graphical user interface, on a mobile device, for collecting health information pertaining to a geographic location that is assigned to the mobile device; causing, at least in part, receiving input, via the mobile device, specifying the health information; and causing, at least in part, initiating transmission of the health information to a disease tracking platform.

According to another embodiment, an apparatus comprising at least one processor, and at least one memory including computer program code, the at least one memory and the computer program code configured to, with the at least one processor, cause the apparatus, at least in part, to initiate presentation of a graphical user interface, on a mobile device, for collecting health information pertaining to a geographic location that is assigned to the mobile device. The apparatus is also caused to, at least in part; receive input, via the mobile device, specifying the health information. The apparatus is further caused to cause, at least in part, initiating transmission of the health information to a disease tracking platform.

According to another embodiment, a computer-readable storage medium carrying one or more sequences of one or more instructions which, when executed by one or more processors, cause an apparatus, at least in part, to initiate presentation of a graphical user interface, on a mobile device, for collecting health information pertaining to a geographic location that is assigned to the mobile device. The apparatus is also caused to, at least in part; receive input, via the mobile device, specifying the health information. The apparatus is further caused to cause, at least in part, initiating transmission of the health information to a disease tracking platform.

According to another embodiment, an apparatus comprises means for causing, at least in part, initiating presentation of a graphical user interface, on a mobile device, for collecting health information pertaining to a geographic location that is assigned to the mobile device. The apparatus also comprises means for causing, at least in part, receiving input, via the mobile device, specifying the health information. The apparatus further comprises means for causing, at least in part, initiating transmission of the health information to a disease tracking platform.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings:

FIG. 7 is a flowchart of a process for collecting, tracking, and disseminating health information, according to one embodiment;

DESCRIPTION OF SOME EMBODIMENTS

A method and apparatus for collecting, tracking and disseminating health information are disclosed. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Figure 1:
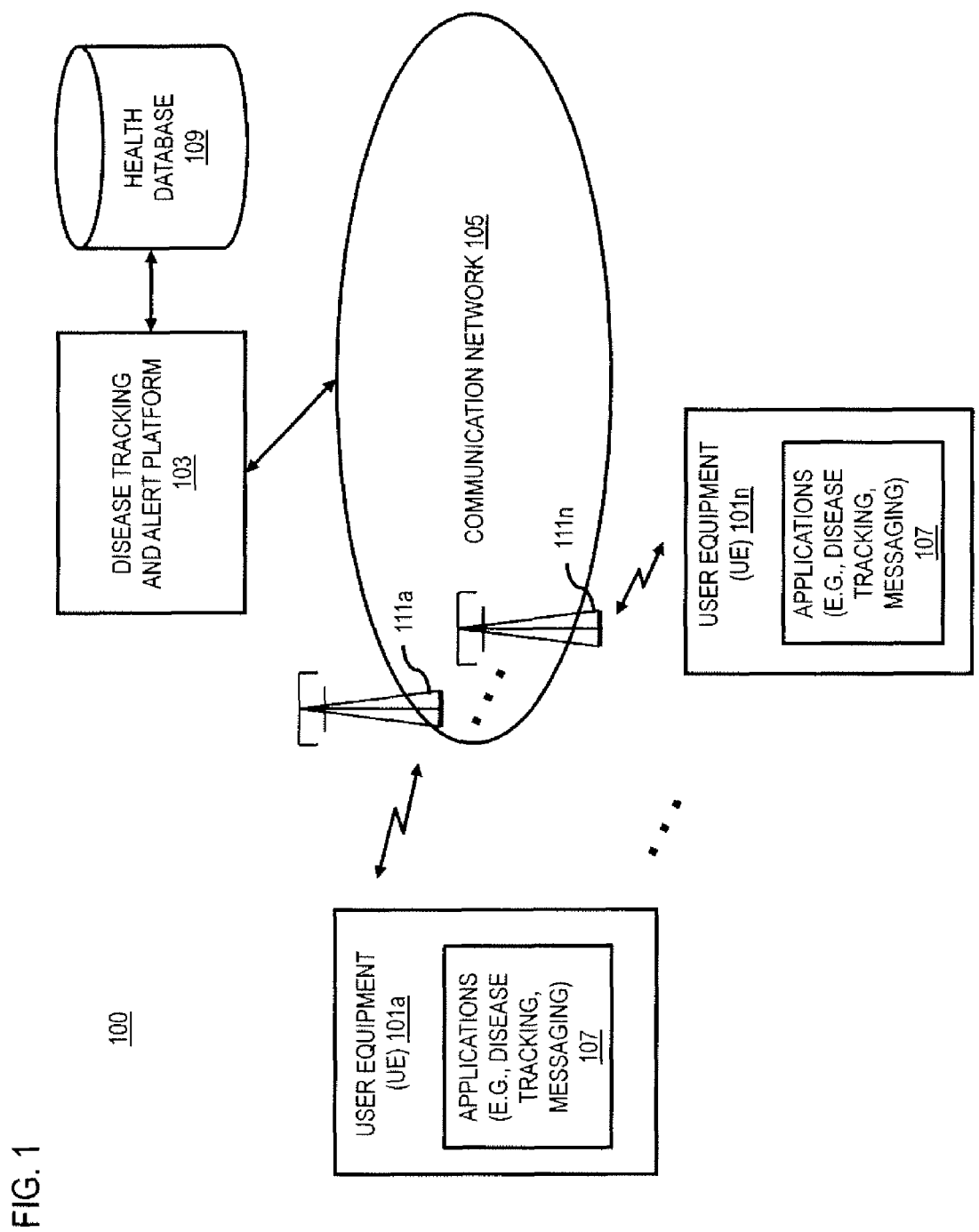
FIG. 1 is a diagram of a system capable of tracking and disseminating health information via mobile channels, according to one embodiment.

FIG. 1 is a diagram of a system 100 capable of collecting, tracking and disseminating health information (e.g., disease information), according to one embodiment. As used herein, disease information may refer to information pertaining to diseases, such as the name of the disease, it's origin, preventative measures, etc. Many countries and agencies desire to track the spread of disease throughout various locations. In many locations, there is difficulty in collecting and tracking disease information as well as quickly communicating the disease information to people to prevent or alleviate the spread of diseases. Health clinics and primary health care providers (e.g., doctors) across the vast locations encounter patients with a range of diseases, from innocuous viruses to highly contagious, life-threatening pandemics. However, the problem with traditional approaches in collecting and tracking diseases relates to the lack of a timely collection mechanism. Consequently, much health related information, such as the daily occurrence of infectious diseases, is reported on paper based forms. Additionally, there is difficulty in disseminating information to people who may be the most affected, once the disease information is collected and analyzed. That is, although the general populace may be aware of the existence of a contagious disease, unless there is greater specificity with regard to who are potentially in harm's way, such information is largely ignored.

The system 100 of FIG. 1 introduces the capability to collect, track and disseminate health information. In one embodiment, user equipment 101, such as mobile devices, can be used to collect health information (e.g., disease information) from health care providers and to effectively disseminate health information to people. In one embodiment, the disease information is collected using one or more user equipment (UE) 101a-101n. Once the disease information is collected, the disease information can be transmitted to a disease tracking and alert platform 103 via a communication network 105. The platform 103, in certain embodiments, provides for the collection of information relating to health threats and diseases, as well as the effective distribution of such information to other organizations or entities for analysis and to people (or users) who may be near or within a zone in which a disease has been discovered or determined to have existed. A user associated with the health care provider (e.g., a doctor, a nurse, a receptionist, etc.) can input the disease information in the UE 101 via a disease tracking application 107. The UE 101 can be any type of mobile terminal, fixed terminal, or portable terminal including a mobile handset, station, unit, device, multimedia tablet, Internet node, communicator, desktop computer, netbook, laptop computer, Personal Digital Assistants (PDAs), or any combination thereof. It is also contemplated that the UE 101 can support any type of interface to the user (such as "wearable" circuitry, etc.).

In another embodiment, once the disease information is received by the disease tracking and alert platform 103, the platform 103 can store the disease information in a health database 109. The disease tracking and alert platform 103 can associate a location of the disease with the disease information based on the user or UE 101 sending the information. For example, a UE 101 possesses a unique identifier, e.g., phone number, can be used to associate the UE 101 with a geographic location. The disease tracking and alert platform 103 can assign (e.g., via registration) the phone number to a geographic location. In one embodiment, the phone numbers can be assigned by a service provided independently from the traditional numbering plan (which specifies a geographic region using, e.g., an area code). Alternatively, the phone numbers from the various area codes can be assigned to their respective geographic locations, per the conventional numbering plan. Once a requisite amount of data is collected, the disease tracking and alert platform 103 can prepare the collected data for analysis; such analysis can be performed in conjunction or independently with another system (e.g., Center for Disease Control and Prevention (CDD), World Heath Organization (WHO), etc.). In some scenarios, the analysis is specific to one or more geographic locations.

Once disease information is analysed, the disease tracking and alert platform 103 can then disseminate the analysis or alert information derived from the analysis to UEs 101. According to certain embodiments, the alert information is provided along with other messages that are destined to the users. In effect, the alert is "piggybacked" onto messages that are already being transmitted to the users without having to generate a separate, distinct message. For example, the alert information can be included as a footer to an existing email to the user. Alternatively, the text of the message, background or foreground, of the message can be altered to provide a visual indicia of the alert. In this manner, network resources are conserved.

In one embodiment, a message that is to be sent to the UE 101 is modified to include the alert information. Also, the alert information can be selectively provided based on the location of the UE 101; in this way, only affected users are notified of a potential health threat. The location of the UE 101 can be provided by the UE 101 itself, or determined by the network. In some scenarios, the message is sent via a text messaging service or an electronic mail service. In other scenarios, the disease tracking and alert platform 103 can send the analysis and/or alert information via a web service.

As shown in FIG. 1, the system 100 comprises a user equipment (UE) 101 having connectivity to the disease tracking and alert platform 103 via a communication network 105. By way of example, the communication network 105 of system 100 includes one or more networks such as a data network (not shown), a wireless network (not shown), a telephony network (not shown), a messaging network (not shown), or any combination thereof. It is contemplated that the data network may be any local area network (LAN), metropolitan area network (MAN), wide area network (WAN), a public data network (e.g., the Internet), or any other suitable packet-switched network, such as a commercially owned, proprietary packet-switched network, e.g., a proprietary cable or fiber-optic network. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, mobile ad-hoc network (MANET), and the like.

Although the disease tracking and alert platform 103 can communicate with the UEs 101a-101n over wireline and wireless technologies, it is recognized that in many locations today (e.g., rural locations, villages, poor areas, etc.), Internet connectivity may not be widely available, and thus, a cellular approach provides ubiquity and convenience to users. Thus, cellular mobile devices can more conveniently collect and disseminate health related information, such as information about contagious diseases within the region.

In one embodiment, a messaging network within the network 105 can provide for SMS messaging, MMS messaging, cell broadcast messaging capabilities, or other messaging capabilities. The messaging network may be a part of a telephony network (e.g., a cellular network). As part of a cellular network, a UE 101 can communicate with a cellular tower 111 to send and receive data including SMS messaging and MMS messaging. Cellular towers 111a-111n can communicate with a UE 101 via control channels so that the UE 101 is able to ascertain which tower to connect to. It is noted that the cellular towers 111a-111n can be associated with a common cellular service provider or multiple cellular providers that are geographically dispersed. A control channel can also be utilized to deliver messages. A message can be sent to a UE 101 via a cellular tower 111 and a message service center (MSC) (not shown). The MSC can be used as a medium between the cellular network and internet protocol networks designed to carry messaging traffic. The message can have information about the message and the destination such as the length of the message, a time stamp, the destination phone number, etc., which can be used to route the message to the destination.

In one example, the disease tracking and alert platform 103 can send a message to the UE 101 via the messaging network by sending the message to the MSC via an internet protocol network. Then, the MSC can deliver the message to the UE 101 via the cellular tower control channel. In another example, the disease tracking and alert platform 103 can send a group of UEs 101 a message via a cell broadcast. With a cell broadcast, the MSC sends the message to a cellular tower 111 and the cellular tower 111, via the cell broadcast, sends the message to each UE 101 connected to the cellular tower 111. Under certain scenarios, the disease tracking and alert platform 103 can send the message to a group of UEs 101 in a geographic location by sending the broadcast via each cellular tower 111 in the geographic location. Alternatively (or additionally), the messaging network can include an email delivery system for alerting users of any health threats or diseases tracked by the platform 103.

By way of example, the UE 101 and disease tracking and alert platform 103 communicate with each other and other components of the communication network 105 using well known, new or still developing protocols. In this context, a protocol includes a set of rules defining how the network nodes within the communication network 105 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application headers (layer 5, layer 6 and layer 7) as defined by the OSI Reference Model.

Figure 2:
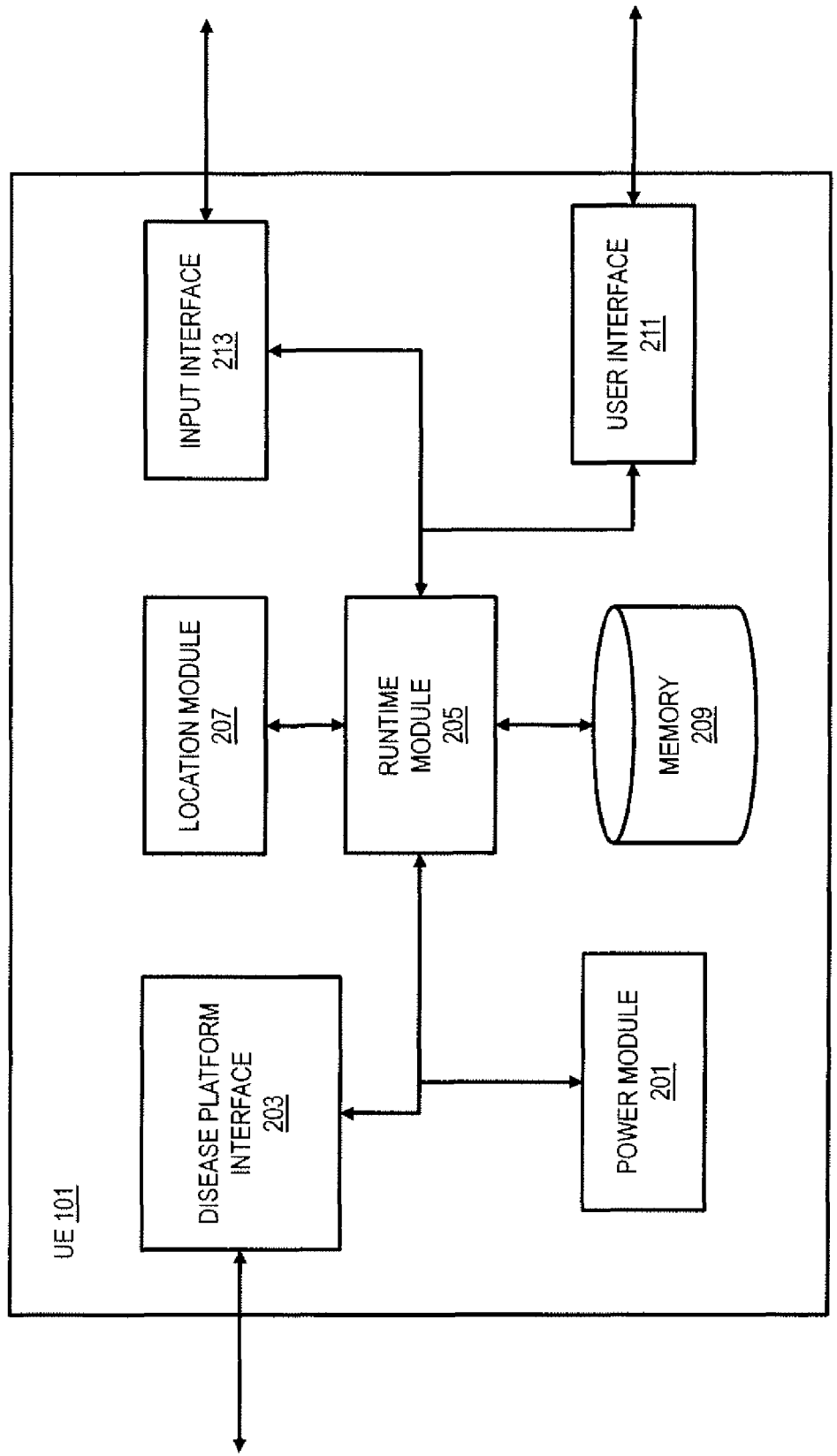
FIG. 2 is a diagram of the components of a user equipment for collecting and presenting health information, according to one embodiment.

FIG. 2 is a diagram of the components of a user equipment 101 for collecting and presenting health information, according to one embodiment. By way of example, the UE 101 includes one or more components for providing collection and presentation of disease information. In one embodiment, the UE 101 can perform analysis of the information. It is contemplated that the functions of these components may be combined in one or more components or performed by other components of equivalent functionality. In this embodiment, the UE 101 includes a power module 201, a disease platform interface 203, a runtime module 205, a location module 207, a memory 209, a user interface 211, and an input interface 213.

In one embodiment, a UE 101 includes a user interface 211. The user interface 211 can include various methods of communication. For example, the user interface 211 can have outputs including a visual component (e.g., a screen), an audio component, a physical component (e.g., vibrations), and other methods of communication. User inputs can include a touch-screen interface, a scroll-and-click interface, a button interface, a microphone, etc. Under one scenario, the visual component or audio component of the user interface 211 can prompt a user (e.g., a doctor) to input information regarding disease information. For example, the user can be prompted, via an interactive voice response system or a graphical presentation, to enter data via a keypad. The user can input the disease information using other user inputs. In another scenario, the visual component can display analysis (e.g., an alert or disease tip) based on a current or a home location of the user. The analysis can be presented in the form of graphs and diagrams, or as other common interfaces (e.g., an e-mail interface or an SMS interface).

In another embodiment, the UE 101 includes an input interface 213. The input interface 213 can include manual user inputs such as a touch-screen interface, a scroll-and-click interface, a button interface, etc. as well as other (e.g., automated) input mechanisms. In one scenario, the UE 101 can receive input from a processor and/or sensor. For instance, a digital image can be captured of a blood sample, and the processor may determine whether the blood sample is positive for a disease (e.g., malaria). It is noted that other biological samples or bodily fluids can be utilized depending on the application—i.e., disease to be tracked. The runtime module 205 can then initiate transmission of the disease information to the disease tracking and alert platform 103 based on a triggering rule (e.g. send an update if a particular disease, such as malaria, is found). In one embodiment, a UE 101 includes a disease platform interface 203. The disease platform interface 203 is used by the runtime module 205 to communicate with the disease tracking and alert platform 103 via various electrical components (e.g., transmitters, receivers, transceivers, etc.). In some embodiments, the disease tracking and alert platform 103 can prompt the runtime module 205 to collect disease information. The runtime module 205 can collect the disease information via the user interface 211 and transmit the disease information to the disease tracking and alert platform 103 via the disease platform interface 203. In other embodiments, the disease tracking and alert platform 103 can provide disease analysis information for the UE 101. The runtime module 205 can receive the analysis and initiate presentation of the analysis via the user interface 211.

In one embodiment, a UE 101 includes a location module 207. This location module 207 can determine a user's location. The user's location can be determined by a triangulation system such as a global positioning system (GPS), A-GPS, Cell of Origin, or other location extrapolation technologies. Standard GPS and A-GPS systems can use satellites to pinpoint the location of a UE 101. A Cell of Origin system can be used to determine the cellular tower that a cellular UE 101 is synchronized with. This information provides a coarse location of the UE 101 because the cellular tower can have a unique cellular identifier (cell-ID) that can be geographically mapped. The location module 207 may also utilize multiple technologies to detect the location of the UE 101. In one embodiment, GPS coordinates and/or a cell-ID are embedded into messages sent to the disease tracking and alert platform 103 to notify the disease tracking and alert platform 103 of the current location of the UE 101.

The power module 201 provides power to the UE 101. The power module 201 can include any type of power source (e.g., battery, plug-in, etc.). Additionally, the power module 201 can provide power to the components of the UE 101 including processors, memory 209, transceivers, or the like.

Figure 3:
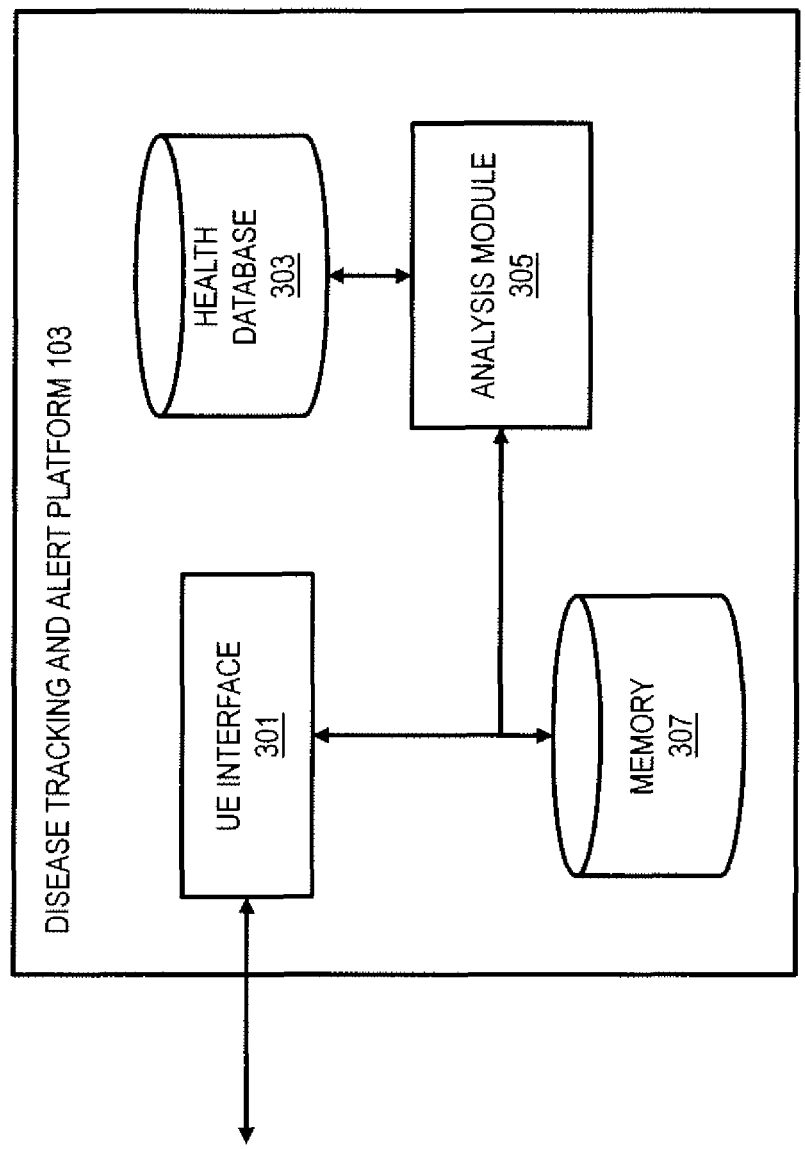
FIG. 3 is a diagram of the components of a disease tracking and alert platform, according to one embodiment.

FIG. 3 is a diagram of the components of a disease tracking and alert platform 103, according to one embodiment. By way of example, the disease tracking and alert platform 103 includes one or more components for tracking, analyzing, and disseminating health information. It is contemplated that the functions of these components may be combined in one or more components or performed by other components of equivalent functionality. In this embodiment, the disease tracking and alert platform 103 includes a UE interface 301, a health database, an analysis module 305, and a memory 307.

In one embodiment, the disease tracking and alert platform 103 includes a UE interface 301. The UE interface 301 can be utilized to communicate to a UE 101 of a user either directly or via platforms and systems. In some examples, the UE interface 301 utilizes electronic components such as transceivers and processors to transmit and receive data to the UE 101. Under some scenarios, the UE interface 301 can include an interactive voice response system, where the UE interface 301 initiates transmission of voice prompts to the UE 101 and receives input responses. Under other scenarios, the UE interface 301 includes initiating transmission (e.g., via messaging infrastructure) of and receiving electronic messaging (e.g., SMS messaging, e-mail, instant messaging, etc.) to the UE 101. In another example, the UE interface 301 includes an interactive web component. The interactive web component can work in conjunction with applications 107 of the UE 101 or via a web interface. In this example, certain UEs 101 (e.g., a doctor) can update information (e.g., update disease information used for analysis in one district) conveyed by the UE interface 301 to other UEs 101 (e.g., a UE 101 of a user interested in disease spread in an area the user wishes to travel to). Additionally, the UE interface 301 can be utilized to send disease information and analysis to research agencies and firms interested in the data.

In another embodiment, the disease tracking and alert platform 103 includes a health database 303 that can be updated by and utilized by an analysis module 305. The analysis module 305 can receive disease information from a UE 101 via the UE interface 301. The analysis module 305 can then store the disease information in a memory 307 and process the disease information to determine a structure to store the disease information in the health database 303. In some embodiments, disease information includes health, location, timing and other disease-related information (e.g., a disease name, a disease strain, etc.) about one or more patients having a disease or other spreadable condition. In one example, the analysis module 305 can retrieve the disease information from a UE 101 and determine that the UE 101 is assigned to a certain geographic location. The analysis module 305 can then store the disease information with information including the assigned geographic location, timing information about when the disease information was taken, and information about the disease involved and the health (e.g., deceased, contagious, the state of the symptoms, etc.) of patients associated with the disease. The analysis module 305 can then retrieve information from the health database and process the information to determine trends and other analysis of the spread of disease using one or more geographic locations. The analysis module 305 can then initiate sending via the UE interface 301 of the analysis and trending information to a UE 101 configured to receive (e.g., via an application 107 or a web interface) the analysis and trending information.

Figures 4A, 4B:
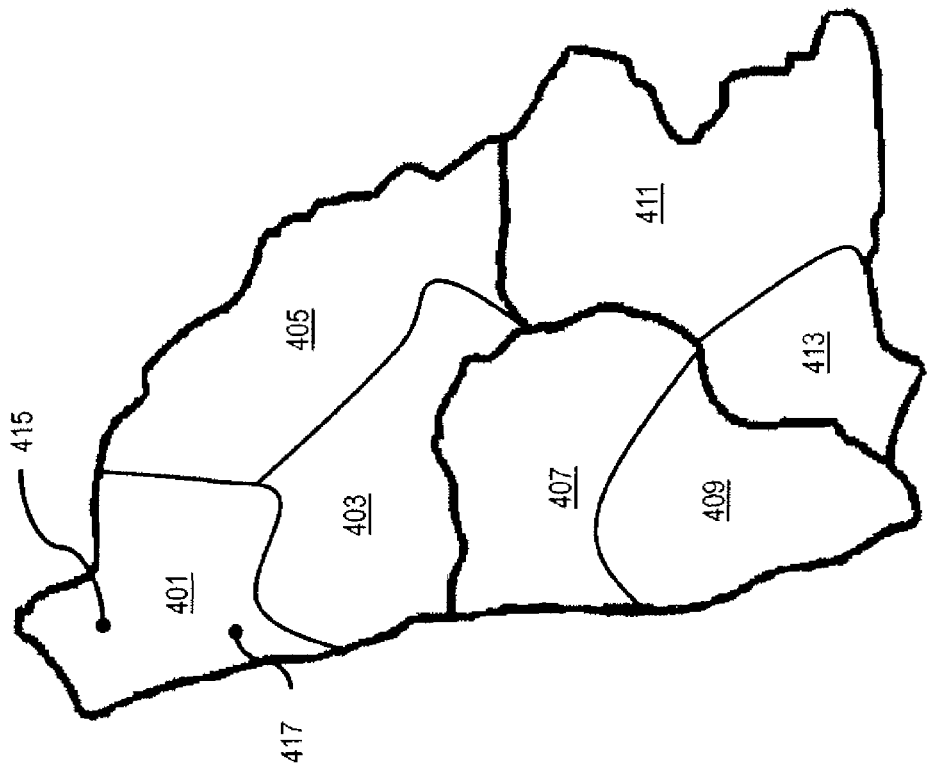
FIGS. 4A and 4B are diagrams of geographic assignments of health centers, according to various embodiments.

FIGS. 4A and 4B are diagrams of geographic assignments of health centers, according to various embodiments. These diagrams can be used to explain a process utilized by the disease tracking and alert platform 103 to assign health centers and UEs 101 for collecting information to geographic locations. The geographic locations can represent health care sub units of a district that be used as a basis to collect and disseminate disease information. FIG. 4A represents a City A, which is divided into districts, for example. The districts are divided into geographic locations that are associated with health centers. Regions 401, 403, and 405 are associated with District A, regions 407 and 409 are associated with District B, and regions 411 and 413 are associated with District C. The districts are further subdivided into geographic locations represented by the regions 401, 403, 405, 407, 409, 411, 413. In certain embodiments, the size and shape of areas can be based on the population of people in those areas.

Each region 401, 403, 405, 407, 409, 411, 413 can be associated with one or more health centers and/or private clinics. In one example, region 401 is associated with a health center. A health center can be a healthcare facility (e.g., a hospital) or a set of healthcare facilities associated with a geographic location. One UE 101 (e.g., a UE 101 of a nurse at a hospital 415) associated with the health center has a phone number of 9900455543. The analysis module 305 can associate the UE 101 with the region 401 during a registration process. Thus, when information is received by a UE 101 associated with the phone number, the analysis module 305 can associate the UE 101 with the phone number and region 401. The phone number can also be used to authenticate the information. Additionally, another UE 101 (e.g., a UE 101 of a doctor at the hospital 415) can be associated with the region 401. The UE 101 can have a separate phone number 9400555555 that is also associated with the region 401 and can be associated with the hospital 415. Further, yet another UE 101 can be associated with a clinic 417 that is also associated with the region 401. This phone number, 9800555555, of the UE 101 can also be assigned to the region 401 by the analysis module 305. The phone numbers for each of the UEs 101 act as a unique identification number to associate the UE 101 with a health center and/or geographic location. The phone numbers can change and be modified using a registration process or an updating process. The unique identification numbers can be used to ensure the authenticity of the source of information as well as to associate the information from the UE 101 with the region 401.

Additionally, in some embodiments, the analysis module 305 can associate GPS coordinates and/or cells with the geographic locations. With this mapping, the analysis module 305 can analyze where a UE 101 is in relation to the geographic locations. This information can be used to help disseminate the information to users to whom the geographic locations are pertinent. These users can be users that are in or around the geographic locations. In one example, a user activates an application 107 to retrieve updates of disease analysis on the user's UE 101. The application 107 can send a request to the analysis module 305 specifying the user's location and requesting analysis surrounding the location. The analysis module 305 can receive the request and determine a mapping of the user's current location and the geographic locations. The analysis module 305 then determines an alert to send the UE 101 giving guidance as to the state of disease spread in the user's current location and/or the state of disease spread in geographic locations within a predetermined range around the user. In one example, the predetermined range is in the form of a distance (e.g., 10 mile radius).

Figure 5:
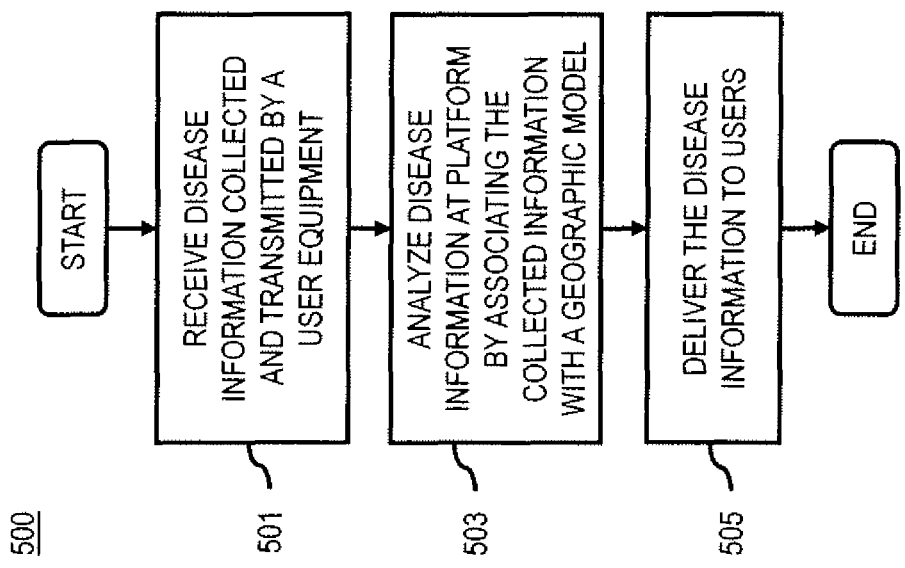
FIG. 5 is a flowchart of a process for collecting, tracking, analyzing, and disseminating disease information, according to one embodiment.

FIG. 5 is a flowchart of a process for collecting, tracking, analyzing, and disseminating disease information, according to one embodiment. In one embodiment, the analysis module 305 of the disease tracking and alert platform 103 performs the process 500 and is implemented in, for instance, a chip set including a processor and a memory as shown FIG. 11. In step 501, the analysis module 305 receives disease information collected and transmitted by a user equipment 101. A phone number associated with the UE 101 can determined by the analysis module 305. The analysis module 305 then associates the disease information with a geographic location as discussed above in the explanation of FIG. 4. The type of disease information being tracked by the disease tracking and alert platform 103 can vary based on the location of the disease tracking and alert platform 103. In one scenario, the diseases being tracked can include various strains of malaria, dengue fever, influenza, cholera, typhoid, etc. In one example, the UE 101 sends disease information about the number of one or more of the tracked diseases diagnosed by the hospital or clinic represented by the UE 101 during the day. For example, the analysis module 305 can receive an SMS from the UE 101 informing the disease tracking and alert platform 103 of 2 new diagnosed cases of malaria, 0 new diagnosed cases of dengue fever, and 8 new cases of influenza A. This disease information can be stored in a health database 303. Additionally, the addition of the disease information can prompt the analysis module 305 to initiate analysis of the health database 303 to account for the new disease information.

At step 503, the analysis module 305 analyzes the disease information by associating the information in the health database 303 with a geographic model. The geographic model can be based on the geographic location assignments discussed in FIG. 4 or based on other methods to associate health centers with geographic locations. The analysis module 305 can select a geographic location or region and analyze the disease information for that geographic location. Additionally or alternatively, the analysis module 305 can determine patterns or the spread of disease over various geographic locations. These patterns can be used to generate alerts to users of UEs 101 in or around geographic locations associated with the analysis.

In one embodiment, at step 505, the analysis module 305 initiates delivering of the disease information and/or analysis to the users. The analysis module 305 can initiate delivery of the analysis in a variety of ways. Under one scenario, a user subscribes to the disease tracking and alert platform 103 by registering with the service. The user can set a home location during the registration process. The analysis module 305 can map the user's home location to geographic locations associated with health centers. Then, when an alert for that geographic location is generated by the analysis module 305, the analysis module 305 initiates transmission (e.g., via an SMS, a message, an e-mail, an interactive web application, etc.) of the alert to the UE 101 of the user. In some examples, the interactive web application can display the alert to the user as a footnote associated with another message. In other examples, the interactive web application is viewed as an e-mail. In one scenario, one or more users subscribe to alerts or periodic information from the disease tracking and alert platform 103. When an alert or a periodic time event is generated for a geographic location, the alert and/or other disease information regarding the geographic location can be sent to one or more UEs 101 associated with the subscriptions.

Figure 6:
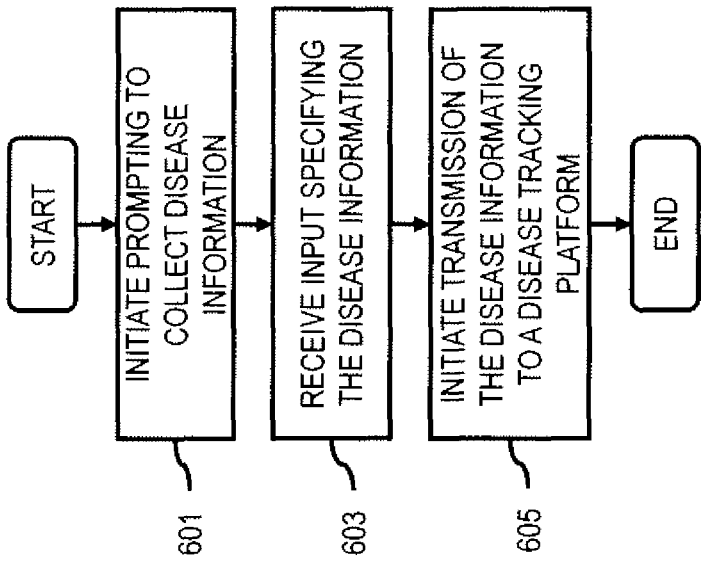
FIG. 6 is a flowchart of a process for collecting health information via a mobile device, according to one embodiment.

FIG. 6 is a flowchart of a process for collecting health information via a mobile device, according to one embodiment. In one embodiment, the runtime module 205 of a UE 101 performs the process 600 and is implemented in, for instance, a chip set including a processor and a memory as shown FIG. 11. A user of UE 101 initiates execution of an input mechanism on the UE 101. Such a mechanism can be a disease tracking application 107 or a voice service.

At step 601, the runtime module 205 initiates prompting to collect disease information. A runtime module 205 of the UE 101 can collect the disease information from a user in various ways. Under one approach, the disease information is collected via the disease tracking application 107. In one embodiment, the runtime module 205 causes, at least in part, the initiation of a presentation of a graphical user interface or an interactive voice response system, on the UE 101 (e.g., a mobile device) for collecting health information pertaining to a geographic location that is assigned to the UE 101. In one example, the health information includes the name of a disease and the amount of cases of the disease diagnosed by the user that day for one or more diseases. Thus, a request for input can include an input for malaria, an input for influenza, and input for dengue fever. The runtime module 205 can prompt the user to input the disease information.

Then, at step 603, the runtime module 205 is caused to, at least in part, receive input, specifying the disease information. The input can be received via a keypad of the UE 101 or another input mechanism. The disease information can be inputted (e.g., by a doctor, a field worker) in response to the prompting for the health information. Under one scenario, a field worker can go to an area (e.g., a rural village) within the assigned geographic location of the UE 101. Alternatively, the UE 101 can track its GPS location and additionally send that information to the disease tracking and alert platform 103 from the area or from another location. A survey or other disease information collection can be performed in these areas and can then be later transmitted. In one embodiment, the disease information can then be formatted in a manner that can be understood by a disease tracking and alert platform 103. For example, the disease information can be formatted as a message (e.g., an SMS) using a predetermined compatible manner (e.g., a data structure including a header, a disease identifier, an input number, and a timestamp) that can be understood by the disease tracking and alert platform 103. The disease tracking and alert platform 103 can be configured to analyze the disease information and use the disease information to modify another message to another UE 101. This can provide the other UE 101 up to date information about the spread of disease in the geographic location associated with the UE 101. For example, the modified other message can include a name of the inputted disease and alerts, warnings, or prevention tips.

In one embodiment, the runtime module 205 receives input specifying disease information from an input interface 213. The input can be a sent by a processor (e.g., a processor associated with a location of the UE 101) that is configured to receive a blood sample and determine if one or more diseases (e.g., malaria) are present in the blood sample. If a disease is present in the blood sample, information about the blood sample (e.g., patient location, patient age, type of disease, etc.) is inputted to the runtime module 205.

Next, at step 605, the runtime module 205 can cause, at least in part, initiation of transmission of the disease information to a disease tracking and alert platform 103. In one example, the transmission is initiated based on a rule that when a certain amount of information is collected about a disease, send an update to the disease tracking and alert platform 103. In another example, a prompt (e.g., in the form of a message) can be displayed to a user of the UE 101 and the user can reply to the prompt to initiate transmission of the information to the disease tracking and alert platform 103. Additionally, the user can initiate sending of the disease information to another contact of the user. In one example, the runtime module 205 initiates transmission of the message to the disease tracking and alert platform 103. In another example, the runtime module 205 utilizes a disease tracking application 107 that is configured to communicate with the disease tracking and alert platform 103. This disease tracking application 107 can send the information to the disease tracking and alert platform 103 via various communications protocols. The disease tracking and alert platform 103 can receive the disease information and analyze the information. Additionally, the disease tracking and alert platform 103 can decipher (e.g., via a telephony caller identification service) a phone number associated with the UE 101 from the communication. The disease tracking and alert platform 103 then associates the UE 101 with the assigned geographic location of the UE 101.

The above approach allows a user of a UE 101 to help track the spread of disease over a geographic area. Many UEs 101 can be utilized to collect information associated with the spread of disease. Additionally, because the UE 101 is associated with a unique identifier, such as phone number, user authorization and location can be based on the phone number. This arrangement can advantageously enable real-time or near real-time collection and dissemination of health related information, as to better initiate the prevention and spread of diseases.

FIG. 7 is a flowchart of a process for collecting, tracking, and disseminating health information, according to one embodiment. In one embodiment, the analysis module 305 of the disease tracking and alert platform 103 performs the process 700 and is implemented in, for instance, a chip set including a processor and a memory as shown FIG. 11. At step 701, the analysis module 305 receives health information from one or more UEs 101 (e.g., mobile devices) corresponding to respective geographic locations. The health information can include disease information about one or more patients. A UE 101 of the UEs 101 can collect and send the health information to the disease tracking and alert platform 103 using various processes (e.g., the processes described in FIG. 6). The analysis module 305 receives the data via various interfaces (e.g., a SMS interface, an interactive voice response system, a web interface, etc.).

At step 703, the analysis module 305 determines a geographic mapping for the UE 101 and health information. The analysis module 305 can assign phone numbers associated with UEs 101 with geographic locations (e.g., in a manner explained in the description of FIGS. 4A and 4B). UEs 101 with assigned phone numbers are authorized to send information to the disease tracking and alert platform 103. When the analysis module 305 receives health information from a UE 101, the analysis module 305 can determine whether the UE 101 is authorized to provide the information. This can be accomplished by determining the phone number of the UE 101 (e.g., via a caller identification service) and comparing the phone number to a list of authorized assigned UEs 101. The analysis module 305 can then determine a geographic location assigned to the UE 101 and associate the received health information with the geographic location. The received health information can be stored in a health database 303.

Then, at step 705, the analysis module 305 can analyze the collected health information. In one example, the health information can include a disease name, a number of diagnosed cases of the disease, the geographic location of the diagnosis, and a timestamp. Statistical algorithms can be used on the collected health information to indicate patterns of disease spread in various geographic locations. One algorithm could associate the number of diagnosed cases of the disease with a location and time information to determine the rate of spread of the disease in the geographic location. Thus, the analysis module 305 can determine if the rate of spread of the disease is accelerating, decelerating, or stable. For instance, the analysis module 305 can determine if there is an upward or downward trend in the occurrence of malaria in a particular geographic location.

In one example, the analysis module 305 can analyze a specific disease using disease information of a geographic location by comparing the geographic location with disease information in adjacent geographic locations. Thus, the analysis module 305 can determine which geographic location in a region or district has the largest number of cases of a particular disease. Additionally, the analysis can be in regards to a percentage of the population having the disease. Moreover, the analysis can determine correlations of two or more diseases in the area. For example, the analysis module 305 can perform an analysis (using statistical modeling and/or an expert system) to determine that an increase in the number of diagnosed cases of a first disease corresponds to (e.g., is a precursor to) the increase of a second disease. An alert to can be generated to warn of the possible threat of the other disease based on the increase in the diagnoses of the first disease.

In another example, the analysis module 305 can analyze a specific disease in a geographic location for signs of an outbreak. A comparison can be made of the reported cases of the disease over the course of a recent time period (e.g., a day, a week, a month, etc.) and a historical time period (e.g., 6 months, 1 year, 5 years, etc.). An outbreak can be predicted if the comparison yields that there is a deviation above a predetermined threshold in the number of recent cases diagnosed in comparison to the rate of diagnosis of the historical cases. In such a scenario, the analysis module 305 can generate an alert to warn of an outbreak.

In yet another example, the analysis module 305 can analyze a specific disease in relation to multiple geographic locations to determine the intensity and direction of the spread of the disease. For example, the analysis module 305 can analyze a recent increase in a disease at a first geographic location at a time two weeks prior. Then, a few days after this increase in the first geographic location 411, the analysis module 305 detects an increase in the diagnosis of cases of the disease in two adjacent geographic locations 403, 405 and a period of time later, additional cases in a geographic location 401 adjacent to those locations 403, 405. This can show that there is a pattern of the disease spreading towards the north and west. The analysis module 305 can generate an alert of this pattern to warn users of the disease tracking and alert platform 103 of the direction of the spread as well as the intensity (e.g., an amount of new diagnoses in relation to the population in each geographic location) of the spread in each of those locations.

In one embodiment, at step 707, the analysis module 305 initiates sending alerts or other health or disease information to a UE 101. The analysis module 305 can send the information to the UE 101 via one or more interfaces (e.g., a messaging interface, a web interface, etc.). Under one scenario, the analysis module 305 can initiate transmission of the multiple users within a geographic location by broadcasting a message via cellular towers within that geographic location. Under another scenario, the interface is a web interface, where the UE 101 has access to the web interface of the disease tracking and alert platform 103 via a disease tracking application 107 or a web browser. In one embodiment, the UE 101 is transmitted the content of the health or disease information or alert via an existing message. The existing message can be related to a service or a group of services associated with the disease tracking and alert platform 103. The analysis module 305 can be routed the message and thus receive a message intended for the UE 101. The disease tracking and alert platform 103 can be an intermediary where a portion of the messages the UE 101 receives is routed through (e.g., via a messaging server). In one example, the message system can be a messaging mechanism using a phone number (which has unique details like country information, operator information, etc. encoded) to route the message. In another example, the message system can utilize web server aspects of the disease tracking and alert platform 103 to send and receive messages in a machine readable language (e.g., using eXtensible Markup Language (XML) tags).

Next, at step 709, the analysis module 305 determines location information associated with the UE 101 configured to receive the message. In one example, the UE 101 can be registered to a tracking service and home location information stored at the disease tracking and alert platform 103. In this example, the home location information can be used to determine the location information. In another example, current location information of the UE 101 can be discerned. The UE 101 can receive updates of the UE 101 current location from the UE 101. In one example, the update can be in the form of a simple data message identifying the UE 101 and GPS coordinates or cell information of the UE 101. The updates can be received from the UE 101 at set periods of time, when the user of the UE 101 transmits an outgoing message, when there is a predetermined magnitude of change in the location information (e.g., moving cell locations or a certain amount of GPS coordinates) of the UE 101, or when there are other triggering events. For example, when a user sends the outgoing message via the disease tracking and alert platform 103 or a platform associated with the disease tracking and alert platform 103, the analysis module 305 can discern the location of the UE 101 by determining the location of the cell at which the UE 101 transmitted the message. This cell information can be contained in the routing information of the message. In a further example, the location information can be used to discern the future location of the UE 101. Multiple GPS coordinates over time can be used to determine a trajectory of the UE 101 and the location information can include a vector. The analysis module 305 can then be use the current location and trajectory information to determine a future location of the UE 101.

At step 711, the analysis module 305 can associate the location information with a geographic location. The geographic location can represent a geographic region associated with a health center (e.g., regions 401, 403, 405 of FIG. 4A). The association can be via mapping the GPS coordinates (e.g., a home location, a current location, or future location) or cell information from the UE 101 to one of the geographic locations representing regions stored in the health database 303. During the mapping process, the analysis module 305 can determine whether the location information of the UE 101 is encompassed by one of the geographic locations. The location information is encompassed by the geographic location if the location information is mapped to the region covered by the geographic location via a mapping rule. A mapping rule could be that if the GPS coordinates or cell identifiers of the UE 101 match a GPS coordinate set or cell identifier set associated with the geographic location, the location information is mapped to the geographic location. In some examples, cell identifiers are mapped to a geographic location even if the entirety of the cell is not completely within the geographic location. Thus, the mapping rule can be based on the proximity of the user to a geographic location. Once the location information is associated with the geographic location, any alerts or information associated with the geographic location can be sent to the user.

Then, at step 713, the message is modified to present a health alert indicator. The health alert indicator can include disease information, alerts in the geographic location, preventative tips, and other health information. The message can be modified by appending supplemental content regarding the alert to the message or by amending the content of the message to include the alert. For example, an alert for a warning can be communicated by modifying the message content to be red. Additionally or alternatively, a footer can be added to the message content so that when the UE 101 presents the message content, the alert is also presented. Then, at step 715, the analysis module 305 causes, at least in part, initiating delivery of the modified message to the UE 101 when the UE 101. The delivery can be via a communication interface between the UE 101 and the disease tracking and alert platform 103. The delivery can occur when the UE 101 is within a predetermined range (e.g., within a set GPS coordinate perimeter) of the geographic location. For example, the delivery can occur before the UE 101 enters the geographic location. Under some scenarios, the analysis module 305 has access to multiple GPS coordinates of the UE 101 and can analyze a route of the UE 101 and determine the location of the next geographic location the UE 101 is heading to and deliver an alert associated with that geographic location.

According to the above approach, a disease tracking and alert platform 103 is able to collect information from a variety of sources associated with geographic locations and analyze the information. Additionally, messages can be dispersed to users using UEs 101 by embedding disease information or alerts in a message already being sent to the UE 101. In this manner, the UE 101 can reduce power consumption of the UE 101 because it need only receive one message to receive the message content and disease information or alert content.

Figure 8:
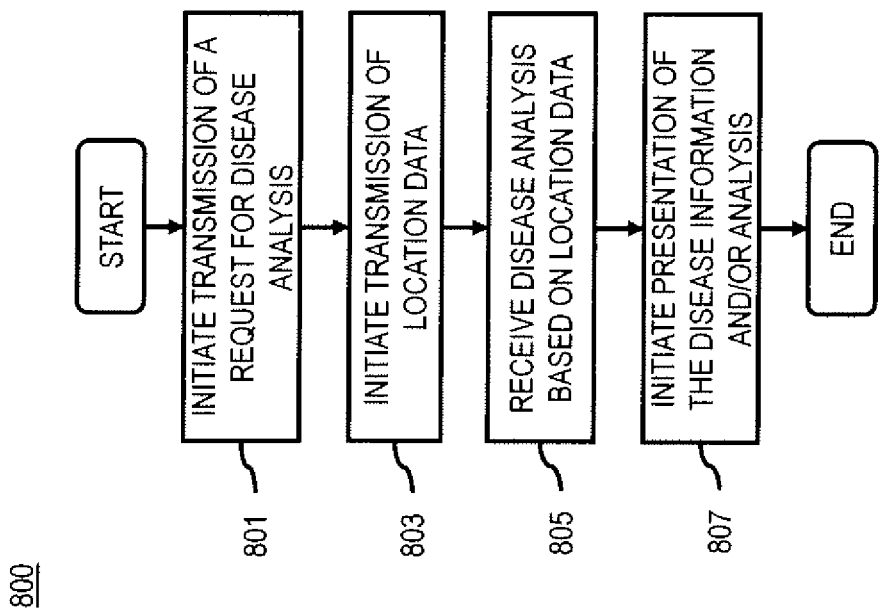
FIG. 8 is a flowchart of a process for receiving and presenting disease information and analysis, according to one embodiment.

FIG. 8 is a flowchart of a process for receiving and presenting disease information and analysis, according to one embodiment. In one embodiment, the runtime module 205 of a UE 101 performs the process 800 and is implemented in, for instance, a chip set including a processor and a memory as shown FIG. 11. The user of the UE 101 can initiate execution of a disease tracking application 107 on the UE 101. The disease tracking application 107 can generate a request specifying a geographic location that the user is interested in receiving disease information or an alert about. At step 801, the UE 101 initiates transmission of the request for disease analysis to the disease tracking and alert platform 103. Additionally or alternatively, the UE 101 can determine a location of the UE 101 using a location module 207 and initiate transfer of the location to the disease tracking and alert platform 103 (step 803). The disease tracking and alert platform 103 can then process the request and send disease information, an analysis and/or alert based on the transmitted location information or the specified geographic location. The UE 101 then receives the disease analysis and/or alert based on the transmitted location (step 805) or the specified geographic location.

In certain scenarios, a user of the UE 101 can subscribe to receive updates or disease information about a specified geographic location or a group of locations. When an alert is generated by the disease tracking and alert platform 103, the alert can be transmitted to the UE 101, which can receive the alert. Additionally or alternatively, updates can be periodic and may include alerts or raw disease information.

Then, at step 807, the runtime module 205 initiates presentation of the disease information and/or analysis. In one example, the runtime module 205 processes the received analysis and/or alert into a graphical presentation. The received data can be in a form that can be parsed by the runtime module 205 and presented via the disease tracking application 107. The disease tracking application 107 can include a routine that displays the received content as a message (e.g., via an inbox), graphs and charts, or other presentation interface.

In one embodiment, a web interface of the disease tracking and alert platform 103 and the UE 101 communicate to provide an advantageous user experience. The web interface can recognize the UE 101 (e.g., based on a phone number) and utilize a presentation specific to that UE 101. The UE 101 receives the presentation via data tags (e.g., XML tags) and can render the tags based on the capabilities of the UE 101. Thus, the tags can be rendered based on the context of the UE 101 (e.g., the processor speed of the UE 101, the display size of the UE 101, the input mechanisms available on the UE 101, etc.). When a presentation is presented to the user, the user may have the option to forward or reply to the message. For example, a reply to the message can be used to start or join a thread commenting on the message or another topic.

Figure 9B:
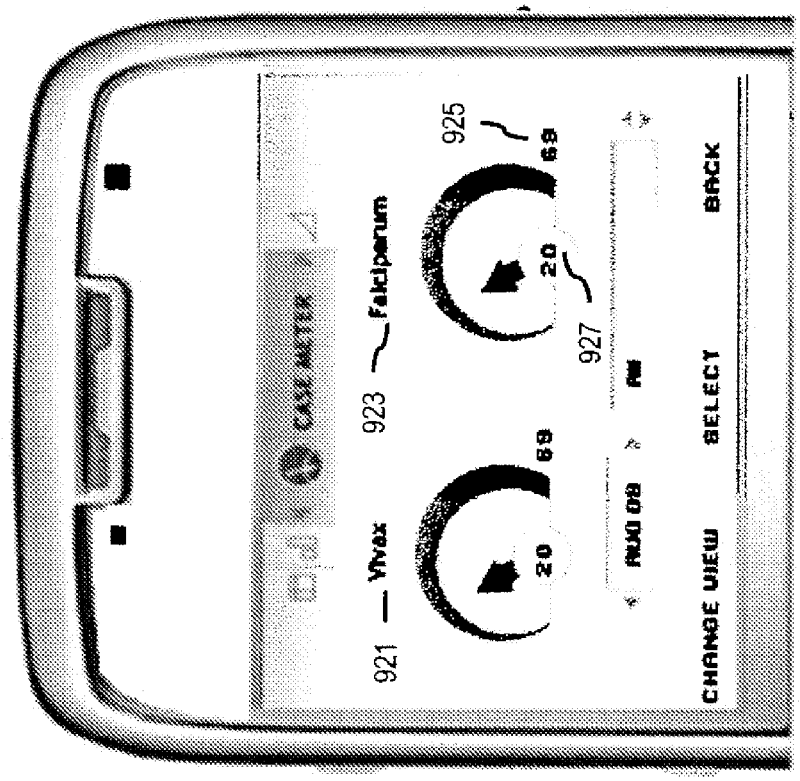
FIGS. 9A-9D are diagrams of user interfaces utilized in the processes of FIGS. 5-8, according to various embodiments.
Figure 9A:
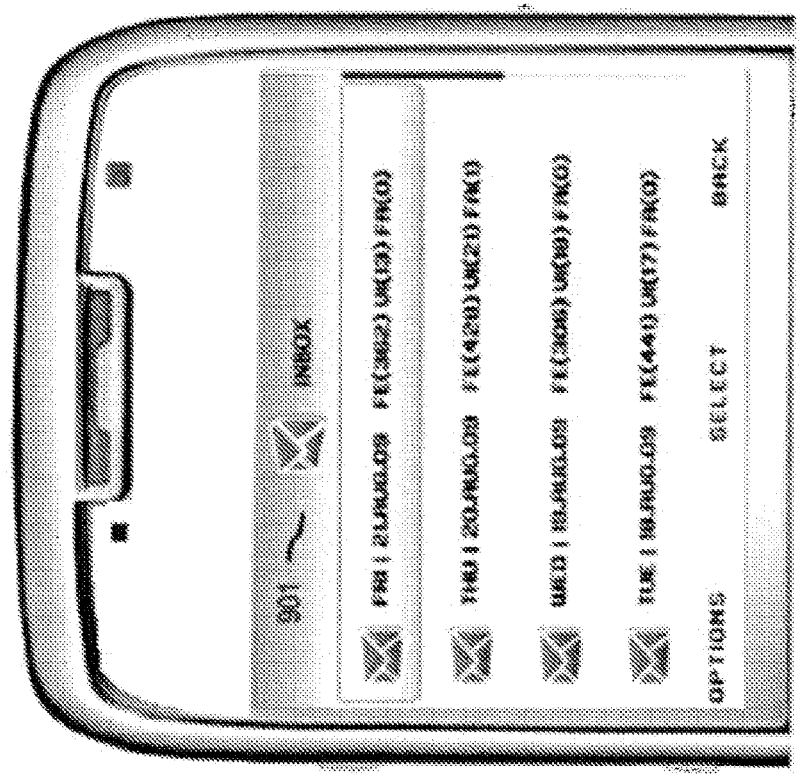

FIGS. 9A-9D are diagrams of user interfaces utilized in the processes of FIG. 8, according to various embodiments. FIG. 9A includes an inbox interface 900 representation of the disease tracking application 107. The inbox can include a set of messages 901 for each day. In certain scenarios, the method used to communicate the information to and from the inbox is a web interface. Thus, even though the user views the presentation as a familiar inbox, the communication medium used to communicate the information is a web channel (e.g., the UE 101 connects to a web server associated with the disease tracking and alert platform 103). Subject lines of the inbox can include a summary of the contents of the day's updated information and/or analysis.

FIG. 9B is a diagram that includes a user interface 920 that displays disease analysis and information in a graphical manner. The interface 920 displays graphs of, e.g., Vivax 921 (a parasite linked with causing malaria) and Falciparum 923 (another parasite linked with causing malaria) cases diagnosed in a geographic location during the month of August. These graphs can indicate the degree and intensity of certain strains of one or more diseases (e.g., strains of malaria caused by Vivax or Falciparum) during the month compared to the historical average number of cases for the month for the associated geographic location. The value 925 indicated at the outer right portion of the semicircle can represent the historic value of the month of August for the geographic location. This is compared to the current value 927 of the diagnosed cases for the month of August. In certain areas, a certain number of disease occurrences can be expected each year. This user interface 920 allows a user to view the disease occurrences for the month of August in perspective to historical data. If the number of occurrences for the current month (e.g., August) outpaces the historic number of occurrences, there may be cause for concern.

Figure 9C:
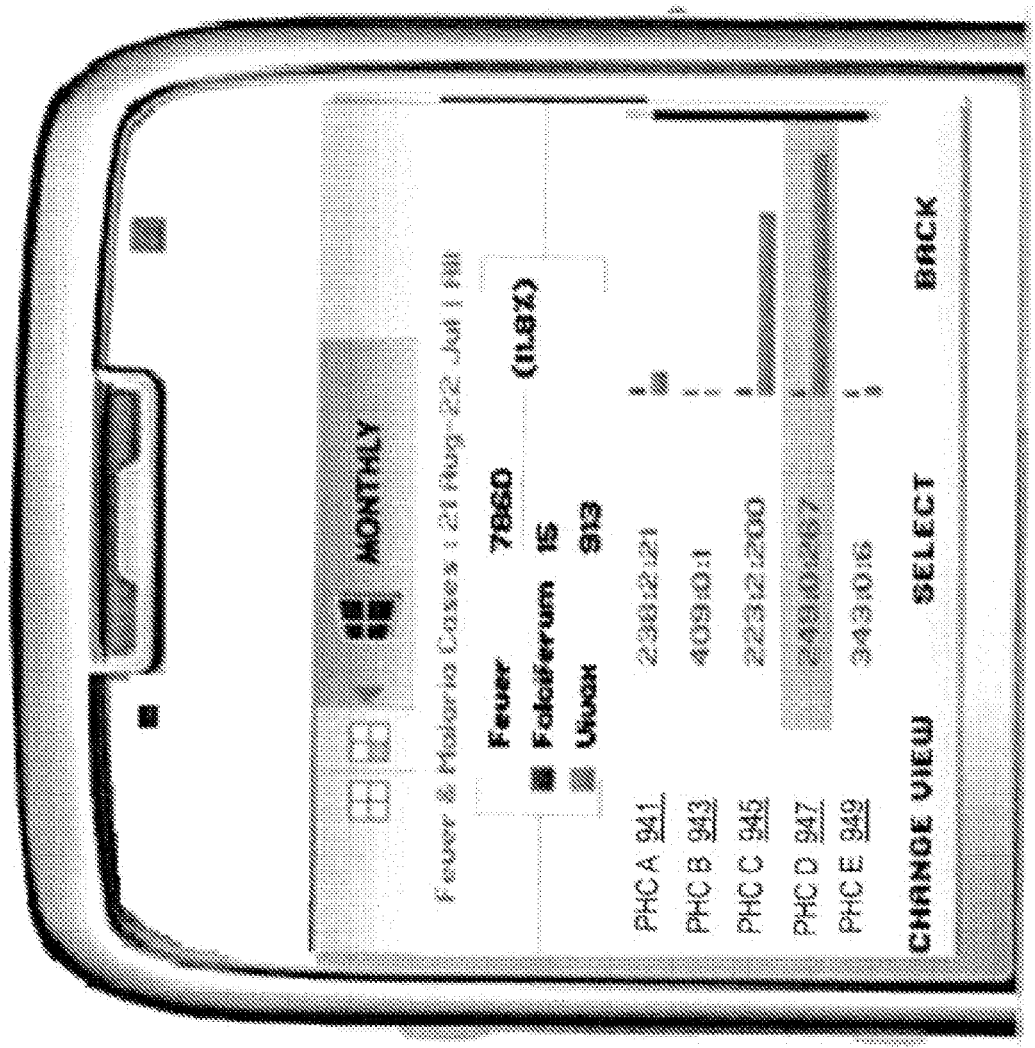

FIG. 9C includes a user interface 940 that is associated with a summary of a month of fever and malaria occurrences associated with geographic locations 941, 943, 945, 947, 949. The summary can show the total amount and the breakdown of fevers, Falciferum, and Vivax of multiple geographic locations 941, 943, 945, 947, 949 during a particular time period (e.g., daily, weekly, monthly, etc.). The summaries can be used by a user to decipher macro trends associated with the diseases by using monthly summaries or micro trends by using daily or weekly summaries.

Figure 9D:
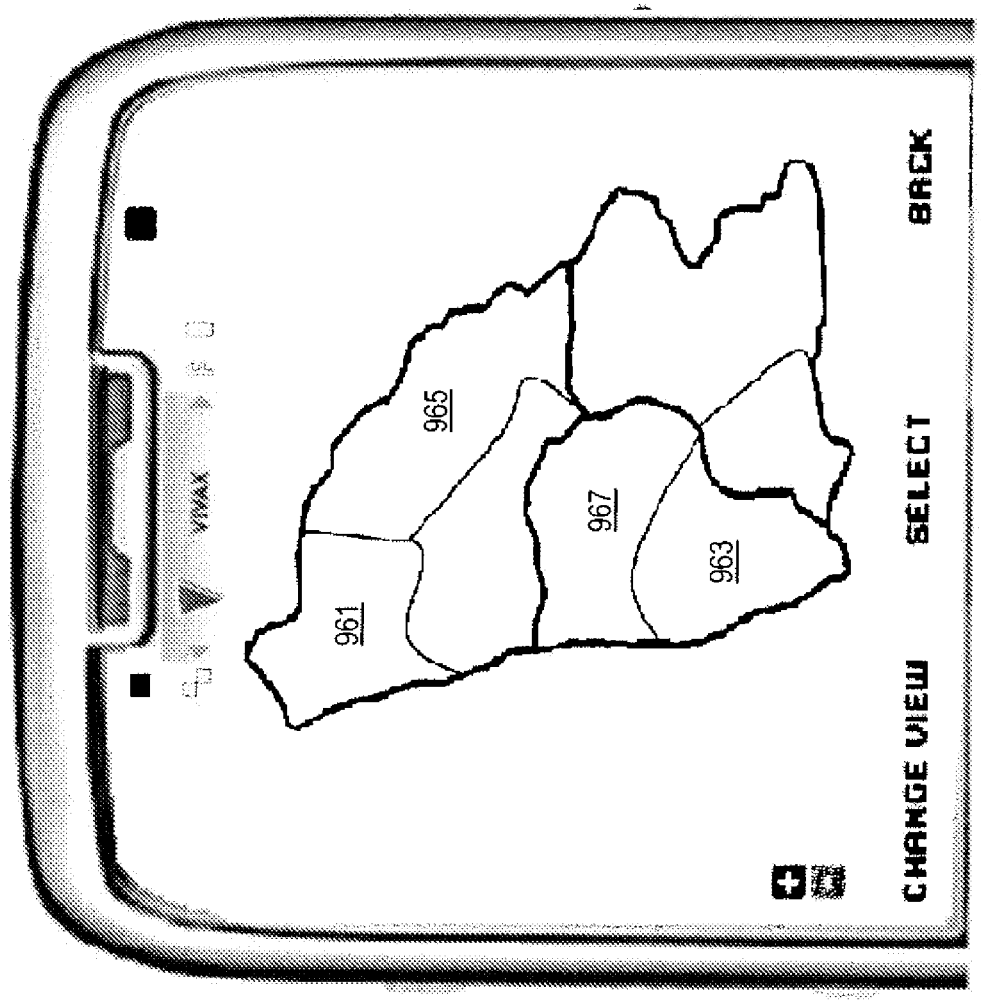

FIG. 9D includes a user interface 960 that displays the occurrences of Vivax in a geographic area. In this scenario, geographic locations 961, 963, 965, 967 can be bounded based on areas associated with health centers. The geographic locations can be color coded representing a level of intensity of cases of Vivax for the month. Geographic location 961 can be colored green reflecting a healthy state with few Vivax occurrences during the month. Geographic location 963 can be colored yellow indicating number of occurrences of Vivax. Geographic location 965 can be colored orange and geographic location 967 can be colored red, reflecting a moderate intensity of the Vivax in the geographic location 965 and a concerning level of intensity of Vivax in geographic location 967. It is contemplated that other geographic disease information may also be presented on a map.

The processes described herein for tracking and disseminating health information may be advantageously implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

Figure 10:
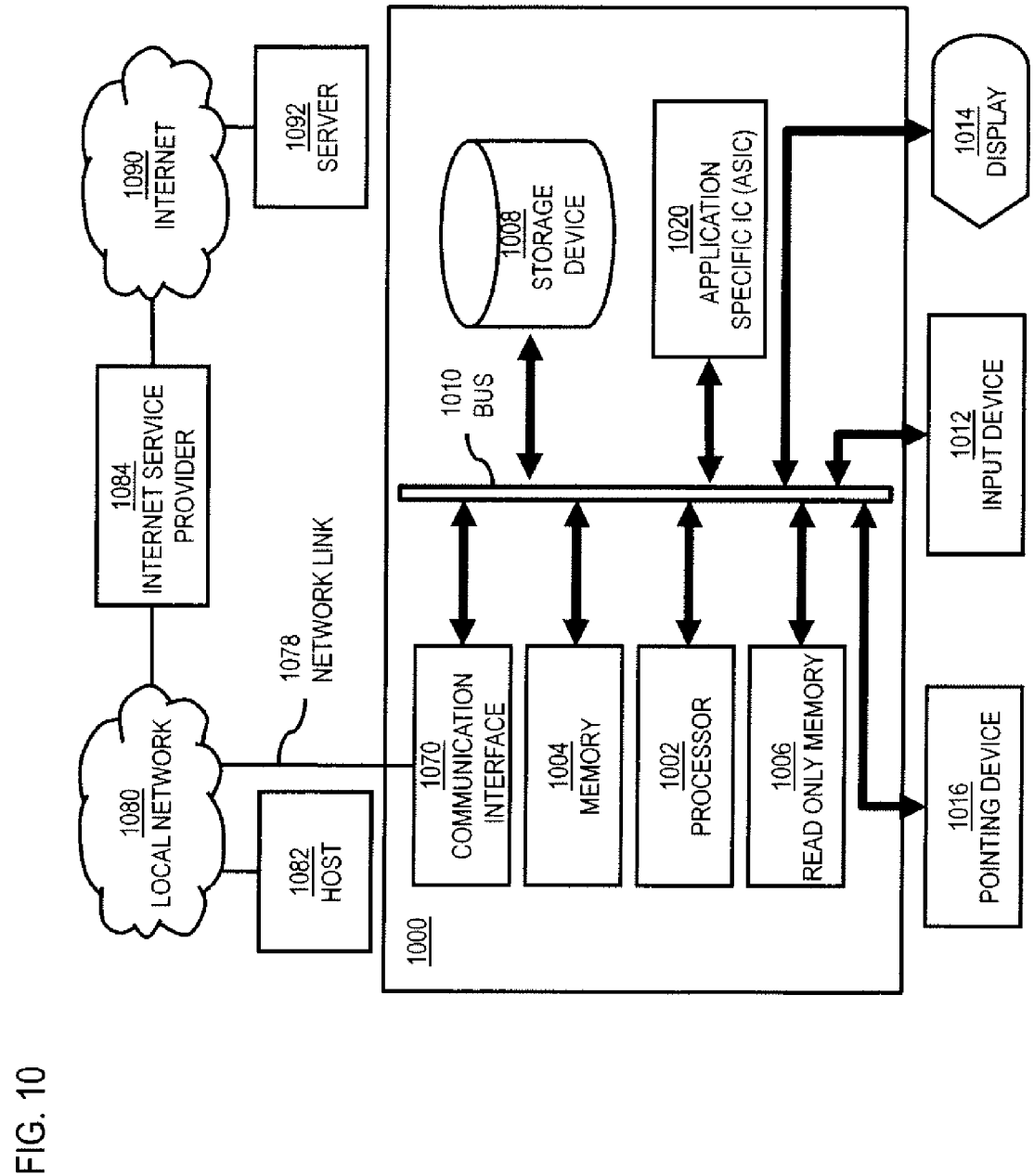
FIG. 10 is a diagram of hardware that can be used to implement an embodiment of the invention.

FIG. 10 illustrates a computer system 1000 upon which an embodiment of the invention may be implemented. Computer system 1000 is programmed (e.g., via computer program code or instructions) to track and disseminate health information as described herein and includes a communication mechanism such as a bus 1010 for passing information between other internal and external components of the computer system 1000. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1000, or a portion thereof, constitutes a means for performing one or more steps of tracking and disseminating health information.

A bus 1010 includes one or more parallel conductors of information so that information is transferred quickly among devices coupled to the bus 1010. One or more processors 1002 for processing information are coupled with the bus 1010.

A processor 1002 performs a set of operations on information as specified by computer program code related to tracking and disseminating health information. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 1010 and placing information on the bus 1010. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 1002, such as a sequence of operation codes, constitute processor instructions, also called computer system instructions or, simply, computer instructions. Processors may be implemented as mechanical, electrical, magnetic, optical, chemical or quantum components, among others, alone or in combination.

Computer system 1000 also includes a memory 1004 coupled to bus 1010. The memory 1004, such as a random access memory (RAM) or other dynamic storage device, stores information including processor instructions for tracking and disseminating health information. Dynamic memory allows information stored therein to be changed by the computer system 1000. RAM allows a unit of information stored at a location called a memory address to be stored and retrieved independently of information at neighboring addresses. The memory 1004 is also used by the processor 1002 to store temporary values during execution of processor instructions. The computer system 1000 also includes a read only memory (ROM) 1006 or other static storage device coupled to the bus 1010 for storing static information, including instructions, that is not changed by the computer system 1000. Some memory is composed of volatile storage that loses the information stored thereon when power is lost. Also coupled to bus 1010 is a non-volatile (persistent) storage device 1008, such as a magnetic disk, optical disk or flash card, for storing information, including instructions, that persists even when the computer system 1000 is turned off or otherwise loses power.

Information, including instructions for tracking and disseminating health information, is provided to the bus 1010 for use by the processor from an external input device 1012, such as a keyboard containing alphanumeric keys operated by a human user, or a sensor. A sensor detects conditions in its vicinity and transforms those detections into physical expression compatible with the measurable phenomenon used to represent information in computer system 1000. Other external devices coupled to bus 1010, used primarily for interacting with humans, include a display device 1014, such as a cathode ray tube (CRT) or a liquid crystal display (LCD), or plasma screen or printer for presenting text or images, and a pointing device 1016, such as a mouse or a trackball or cursor direction keys, or motion sensor, for controlling a position of a small cursor image presented on the display 1014 and issuing commands associated with graphical elements presented on the display 1014. In some embodiments, for example, in embodiments in which the computer system 1000 performs all functions automatically without human input, one or more of external input device 1012, display device 1014 and pointing device 1016 is omitted.

In the illustrated embodiment, special purpose hardware, such as an application specific integrated circuit (ASIC) 1020, is coupled to bus 1010. The special purpose hardware is configured to perform operations not performed by processor 1002 quickly enough for special purposes. Examples of application specific ICs include graphics accelerator cards for generating images for display 1014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1000 also includes one or more instances of a communications interface 1070 coupled to bus 1010. Communication interface 1070 provides a one-way or two-way communication coupling to a variety of external devices that operate with their own processors, such as printers, scanners and external disks. In general the coupling is with a network link 1078 that is connected to a local network 1080 to which a variety of external devices with their own processors are connected. For example, communication interface 1070 may be a parallel port or a serial port or a universal serial bus (USB) port on a personal computer. In some embodiments, communications interface 1070 is an integrated services digital network (ISDN) card or a digital subscriber line (DSL) card or a telephone modem that provides an information communication connection to a corresponding type of telephone line. In some embodiments, a communication interface 1070 is a cable modem that converts signals on bus 1010 into signals for a communication connection over a coaxial cable or into optical signals for a communication connection over a fiber optic cable. As another example, communications interface 1070 may be a local area network (LAN) card to provide a data communication connection to a compatible LAN, such as Ethernet. Wireless links may also be implemented. For wireless links, the communications interface 1070 sends or receives or both sends and receives electrical, acoustic or electromagnetic signals, including infrared and optical signals, that carry information streams, such as digital data. For example, in wireless handheld devices, such as mobile telephones like cell phones, the communications interface 1070 includes a radio band electromagnetic transmitter and receiver called a radio transceiver. In certain embodiments, the communications interface 1070 enables connection to the communication network 105 for collecting and disseminating health information from/to the UE 101.

The term computer-readable medium is used herein to refer to any medium that participates in providing information to processor 1002, including instructions for execution. Such a medium may take many forms, including, but not limited to, non-volatile media, volatile media and transmission media. Non-volatile media include, for example, optical or magnetic disks, such as storage device 1008. Volatile media include, for example, dynamic memory 1004. Transmission media include, for example, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 1020.

Network link 1078 typically provides information communication using transmission media through one or more networks to other devices that use or process the information. For example, network link 1078 may provide a connection through local network 1080 to a host computer 1082 or to equipment 1084 operated by an Internet Service Provider (ISP). ISP equipment 1084 in turn provides data communication services through the public, world-wide packet-switching communication network of networks now commonly referred to as the Internet 1090. A computer called a server host 1092 connected to the Internet hosts a process that provides a service in response to information received over the Internet. For example, server host 1092 hosts a process that provides information representing video data for presentation at display 1014.

At least some embodiments of the invention are related to the use of computer system 1000 for implementing some or all of the techniques described herein. According to one embodiment of the invention, those techniques are performed by computer system 1000 in response to processor 1002 executing one or more sequences of one or more processor instructions contained in memory 1004. Such instructions, also called computer instructions, software and program code, may be read into memory 1004 from another computer-readable medium such as storage device 1008 or network link 1078. Execution of the sequences of instructions contained in memory 1004 causes processor 1002 to perform one or more of the method steps described herein. In alternative embodiments, hardware, such as ASIC 1020, may be used in place of or in combination with software to implement the invention. Thus, embodiments of the invention are not limited to any specific combination of hardware and software, unless otherwise explicitly stated herein.

The signals transmitted over network link 1078 and other networks through communications interface 1070, carry information to and from computer system 1000. Computer system 1000 can send and receive information, including program code, through the networks 1080, 1090 among others, through network link 1078 and communications interface 1070. In an example using the Internet 1090, a server host 1092 transmits program code for a particular application, requested by a message sent from computer 1000, through Internet 1090, ISP equipment 1084, local network 1080 and communications interface 1070. The received code may be executed by processor 1002 as it is received, or may be stored in memory 1004 or in storage device 1008 or other non-volatile storage for later execution, or both. In this manner, computer system 1000 may obtain application program code in the form of signals on a carrier wave.

Various forms of computer readable media may be involved in carrying one or more sequence of instructions or data or both to processor 1002 for execution. For example, instructions and data may initially be carried on a magnetic disk of a remote computer such as host 1082. The remote computer loads the instructions and data into its dynamic memory and sends the instructions and data over a telephone line using a modem. A modem local to the computer system 1000 receives the instructions and data on a telephone line and uses an infra-red transmitter to convert the instructions and data to a signal on an infra-red carrier wave serving as the network link 1078. An infrared detector serving as communications interface 1070 receives the instructions and data carried in the infrared signal and places information representing the instructions and data onto bus 1010. Bus 1010 carries the information to memory 1004 from which processor 1002 retrieves and executes the instructions using some of the data sent with the instructions. The instructions and data received in memory 1004 may optionally be stored on storage device 1008, either before or after execution by the processor 1002.

Figure 11:
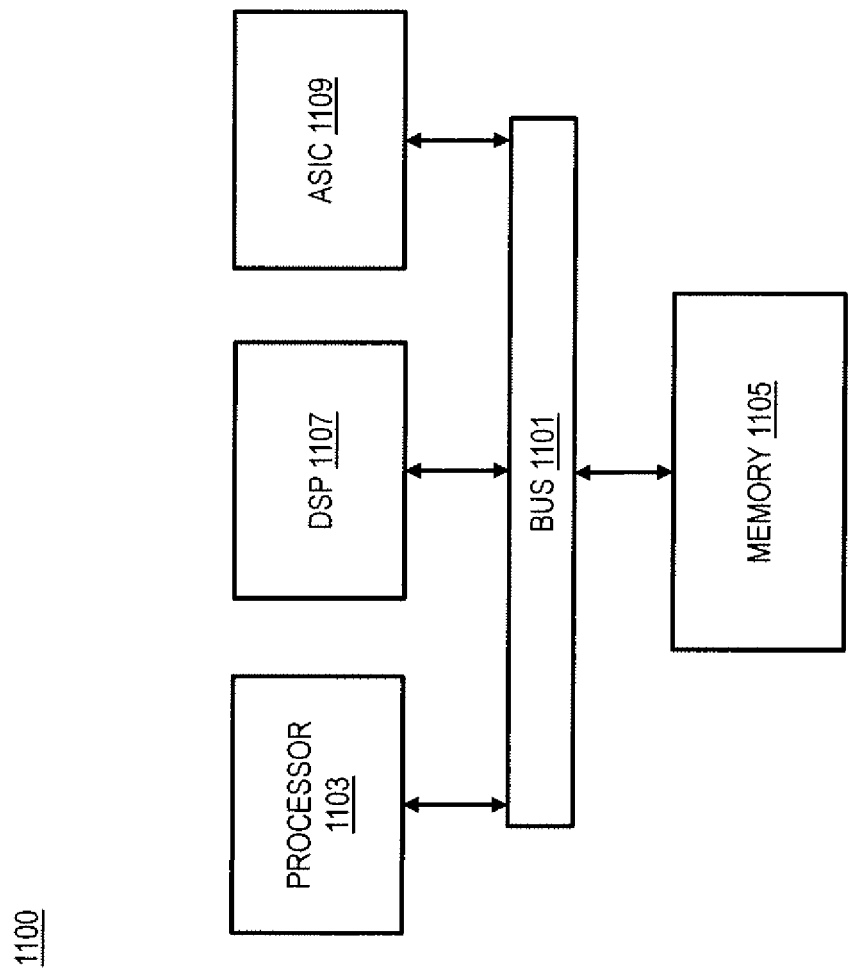
FIG. 11 is a diagram of a chip set that can be used to implement an embodiment of the invention.

FIG. 11 illustrates a chip set 1100 upon which an embodiment of the invention may be implemented. Chip set 1100 is programmed to track and disseminate health information as described herein and includes, for instance, the processor and memory components described with respect to FIG. 10 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1100, or a portion thereof, constitutes a means for performing one or more steps of tracking and disseminating health information.

In one embodiment, the chip set 1100 includes a communication mechanism such as a bus 1101 for passing information among the components of the chip set 1100. A processor 1103 has connectivity to the bus 1101 to execute instructions and process information stored in, for example, a memory 1105. The processor 1103 may include one or more processing cores with each core configured to perform independently. A multi-core processor enables multiprocessing within a single physical package. Examples of a multi-core processor include two, four, eight, or greater numbers of processing cores. Alternatively or in addition, the processor 1103 may include one or more microprocessors configured in tandem via the bus 1101 to enable independent execution of instructions, pipelining, and multithreading. The processor 1103 may also be accompanied with one or more specialized components to perform certain processing functions and tasks such as one or more digital signal processors (DSP) 1107, or one or more application-specific integrated circuits (ASIC) 1109. A DSP 1107 typically is configured to process real-world signals (e.g., sound) in real time independently of the processor 1103. Similarly, an ASIC 1109 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1103 and accompanying components have connectivity to the memory 1105 via the bus 1101. The memory 1105 includes both dynamic memory (e.g., RAM, magnetic disk, writable optical disk, etc.) and static memory (e.g., ROM, CD-ROM, etc.) for storing executable instructions that when executed perform the inventive steps described herein to track and disseminate health information. The memory 1105 also stores the data associated with or generated by the execution of the inventive steps.

Figure 12:
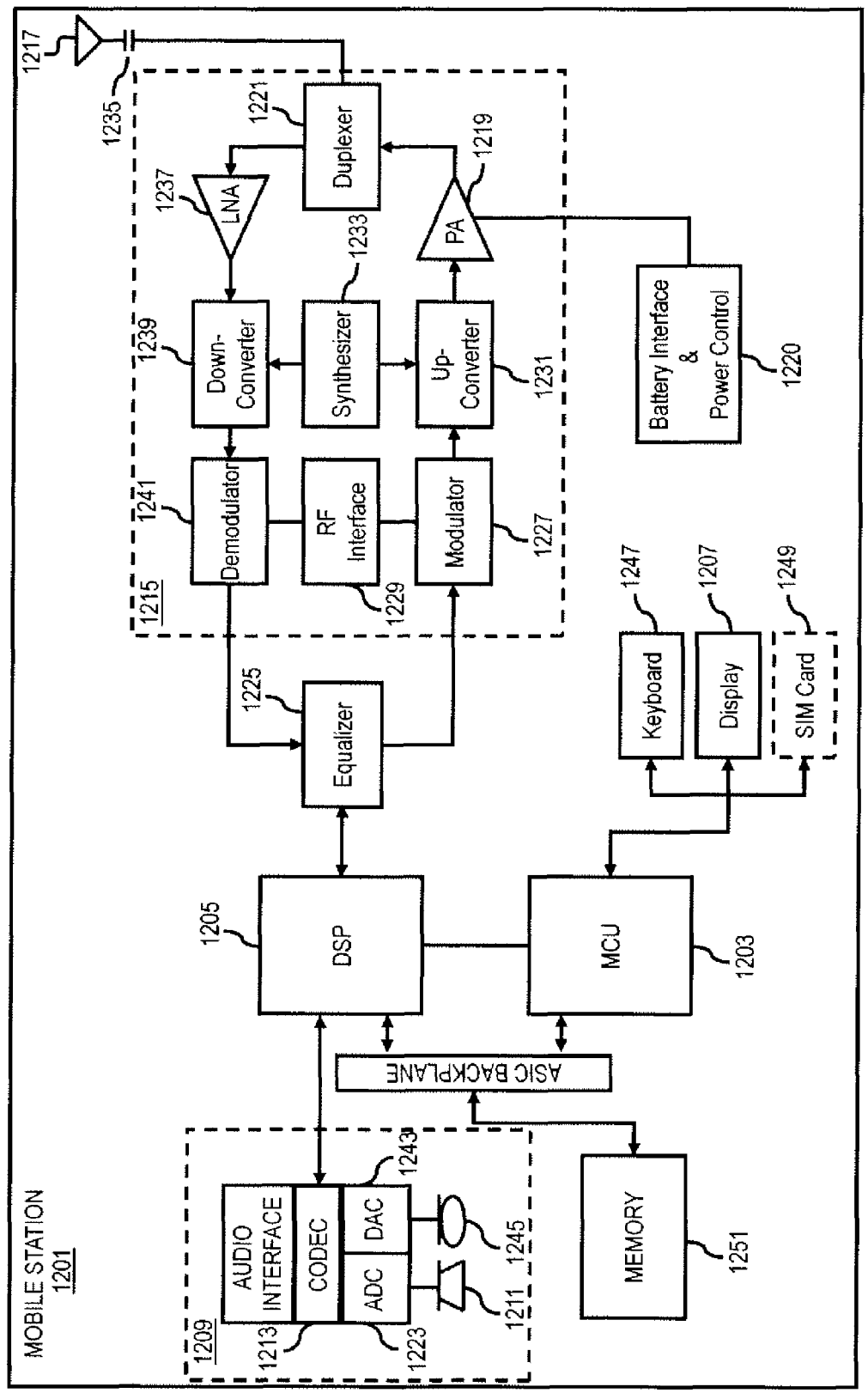
FIG. 12 is a diagram of a mobile terminal (e.g., handset) that can be used to implement an embodiment of the invention.

FIG. 12 is a diagram of exemplary components of a mobile terminal (e.g., handset) for communications, which is capable of operating in the system of FIG. 1, according to one embodiment. In some embodiments, mobile terminal 1200, or a portion thereof, constitutes a means for performing one or more steps of tracking and disseminating health information. Generally, a radio receiver is often defined in terms of front-end and back-end characteristics. The front-end of the receiver encompases all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application, the term "circuitry" would also cover an implementation of merely a processor (or multiple processors) and its (or their) accompanying software/or firmware. The term "circuitry" would also cover, for example, a baseband integrated circuit or applications processor integrated circuit in a mobile phone or a similar integrated circuit in a cellular network device or other network devices.

Pertinent internal components of the telephone include a Main Control Unit (MCU) 1203, a Digital Signal Processor (DSP) 1205, and a receiver/transmitter unit including a microphone gain control unit and a speaker gain control unit. A main display unit 1207 provides a display to the user in support of various applications and mobile terminal functions that perform or support the steps of tracking and disseminating health information. The display unit 1207 includes display circuitry configured to display at least a portion of a user interface of the mobile terminal (e.g., mobile telephone). Additionally, the display unit 1207 and display circuitry are configured to facilitate user control of at least some functions of the mobile terminal. An audio function circuitry 1209 includes a microphone 1211 and microphone amplifier that amplifies the speech signal output from the microphone 1211. The amplified speech signal output from the microphone 1211 is fed to a coder/decoder (CODEC) 1213.

A radio section 1215 amplifies power and converts frequency in order to communicate with a base station, which is included in a mobile communication system, via antenna 1217. The power amplifier (PA) 1219 and the transmitter/modulation circuitry are operationally responsive to the MCU 1203, with an output from the PA 1219 coupled to the duplexer 1221 or circulator or antenna switch, as known in the art. The PA 1219 also couples to a battery interface and power control unit 1220.

In use, a user of mobile terminal 1201 speaks into the microphone 1211 and his or her voice along with any detected background noise is converted into an analog voltage. The analog voltage is then converted into a digital signal through the Analog to Digital Converter (ADC) 1223. The control unit 1203 routes the digital signal into the DSP 1205 for processing therein, such as speech encoding, channel encoding, encrypting, and interleaving. In one embodiment, the processed voice signals are encoded, by units not separately shown, using a cellular transmission protocol such as global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like.

The encoded signals are then routed to an equalizer 1225 for compensation of any frequency-dependent impairments that occur during transmission though the air such as phase and amplitude distortion. After equalizing the bit stream, the modulator 1227 combines the signal with a RF signal generated in the RF interface 1229. The modulator 1227 generates a sine wave by way of frequency or phase modulation. In order to prepare the signal for transmission, an up-converter 1231 combines the sine wave output from the modulator 1227 with another sine wave generated by a synthesizer 1233 to achieve the desired frequency of transmission. The signal is then sent through a PA 1219 to increase the signal to an appropriate power level. In practical systems, the PA 1219 acts as a variable gain amplifier whose gain is controlled by the DSP 1205 from information received from a network base station. The signal is then filtered within the duplexer 1221 and optionally sent to an antenna coupler 1235 to match impedances to provide maximum power transfer. Finally, the signal is transmitted via antenna 1217 to a local base station. An automatic gain control (AGC) can be supplied to control the gain of the final stages of the receiver. The signals may be forwarded from there to a remote telephone which may be another cellular telephone, other mobile phone or a land-line connected to a Public Switched Telephone Network (PSTN), or other telephony networks.

Voice signals transmitted to the mobile terminal 1201 are received via antenna 1217 and immediately amplified by a low noise amplifier (LNA) 1237. A down-converter 1239 lowers the carrier frequency while the demodulator 1241 strips away the RF leaving only a digital bit stream. The signal then goes through the equalizer 1225 and is processed by the DSP 1205. A Digital to Analog Converter (DAC) 1243 converts the signal and the resulting output is transmitted to the user through the speaker 1245, all under control of a Main Control Unit (MCU) 1203—which can be implemented as a Central Processing Unit (CPU) (not shown).

The MCU 1203 receives various signals including input signals from the keyboard 1247. The keyboard 1247 and/or the MCU 1203 in combination with other user input components (e.g., the microphone 1211) comprise a user interface circuitry for managing user input. The MCU 1203 runs a user interface software to facilitate user control of at least some functions of the mobile terminal 1201 to track and disseminate health information. The MCU 1203 also delivers a display command and a switch command to the display 1207 and to the speech output switching controller, respectively. Further, the MCU 1203 exchanges information with the DSP 1205 and can access an optionally incorporated SIM card 1249 and a memory 1251. In addition, the MCU 1203 executes various control functions required of the terminal. The DSP 1205 may, depending upon the implementation, perform any of a variety of conventional digital processing functions on the voice signals. Additionally, DSP 1205 determines the background noise level of the local environment from the signals detected by microphone 1211 and sets the gain of microphone 1211 to a level selected to compensate for the natural tendency of the user of the mobile terminal 1201.

The CODEC 1213 includes the ADC 1223 and DAC 1243. The memory 1251 stores various data including call incoming tone data and is capable of storing other data including music data received via, e.g., the global Internet. The software module could reside in RAM memory, flash memory, registers, or any other form of writable storage medium known in the art. The memory device 1251 may be, but not limited to, a single memory, CD, DVD, ROM, RAM, EEPROM, optical storage, or any other non-volatile storage medium capable of storing digital data.

An optionally incorporated SIM card 1249 carries, for instance, important information, such as the cellular phone number, the carrier supplying service, subscription details, and security information. The SIM card 1249 serves primarily to identify the mobile terminal 1201 on a radio network. The card 1249 also contains a memory for storing a personal telephone number registry, text messages, and user specific mobile terminal settings.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. A method comprising:
    analyzing health information corresponding to a receiving geographic location with respect to a collecting geographic location, wherein the collecting geographic location is mapped to one or more identifiers associated with a collecting user equipment, wherein the one or more identifiers are telephone numbers of one or more mobile devices, and wherein the collecting geographic location is independent of area code information of the telephone numbers;

issuing a health alert indicator based, at least in part, on the analysis of the health information to a receiving user equipment when the receiving user equipment is determined to be in or within a predetermined range of the collecting geographic location;

amending or appending supplemental content to the health alert indicator for the receiving geographic location when the receiving user equipment is determined to be in or within the receiving geographic location; and delivering the amended or supplemented health alert indicator to the receiving user equipment when the receiving user equipment is in or within a predetermined range of the collecting geographic location.

2. A method of claim 1, wherein the supplemental content specifies a name of a disease associated with the health information.

3. An apparatus comprising:

at least one processor; and at least one memory including computer program code for one or more programs, the at least one memory and the computer program code configured to, with the at least one processor, cause the apparatus to perform at least the following:

analyze health information corresponding to a receiving geographic location with respect to a collecting geographic location, wherein the collecting geographic location is mapped to one or more identifiers associated with a collecting user equipment, wherein the one or more identifiers are telephone numbers of one or more mobile devices, and wherein the collecting geographic location is independent of area code information of the telephone numbers;

issue a health alert indicator based, at least in part, on the analysis of the health information to a receiving user equipment when the receiving user equipment is determined to be in or within a predetermined ranged of the collecting geographic location;

amend or append supplemental content to the health alert indicator for the receiving geographic location when the receiving user equipment is determined to be in or within the receiving geographic location; and deliver the amended or supplemented health alert indicator to the receiving user equipment when the receiving user equipment is in or within a predetermined range of the collecting geographic location.

4. An apparatus of claim 3, wherein the supplemental content specifies a name of a disease associated with the health information.

5. A non-transitory computer storage medium carrying one or more sequences of one or more instructions which, when executed by one or more processors, cause an apparatus to perform:

analyzing health information corresponding to a receiving geographic location with respect to a collecting geographic location, wherein the collecting geographic location is mapped to one or more identifiers associated with a collecting user equipment, wherein the one or more identifiers are telephone numbers of one or more mobile devices, and wherein the collecting geographic location is independent of area code information of the telephone numbers;

issuing a health alert indicator based, at least in part, on the analysis of the health information to a receiving user equipment when the receiving user equipment is determined to be in or within a predetermined range of the collecting geographic location;

amending or appending supplemental content to the health alert indicator for the receiving geographic location when the receiving user equipment is determined to be in or within the receiving geographic location; and delivering the amended or supplemented health alert indicator to the receiving user equipment when the receiving user equipment is in or within a predetermined range of the collecting geographic location.

6. A non-transitory computer storage medium of claim 5, wherein the supplemental content specifies a name of a disease associated with the health information.

* * * * *